(12) United States Patent
Lopez et al.

(10) Patent No.: US 8,282,641 B2
(45) Date of Patent: Oct. 9, 2012

(54) METHODS AND INSTRUMENTATION FOR DISC REPLACEMENT

(75) Inventors: Erasmo Lopez, Seattle, WA (US); Jonathan Bellas, Bridgewater, MA (US); Amie Borgstrom, Stanford, CA (US); Douglas R. LaSota, Saugus, MA (US)

(73) Assignee: DePuy Spine, Inc., Raynham, MA (US)

( * ) Notice: Subject to any disclaimer, the term of this patent is extended or adjusted under 35 U.S.C. 154(b) by 1153 days.

(21) Appl. No.: 11/776,819

(22) Filed: Jul. 12, 2007

(65) Prior Publication Data

US 2008/0051897 A1 Feb. 28, 2008

Related U.S. Application Data

(63) Continuation-in-part of application No. 11/277,726, filed on Mar. 28, 2006, and a continuation-in-part of application No. 11/277,725, filed on Mar. 28, 2006.

(60) Provisional application No. 60/807,397, filed on Jul. 14, 2006.

(51) Int. Cl.
*A61B 17/70* (2006.01)
(52) U.S. Cl. ..... 606/86 A; 606/249; 606/263; 623/17.16
(58) Field of Classification Search .... 623/17.11–17.16; 606/246, 279, 249, 251–253, 263, 86 A
See application file for complete search history.

(56) References Cited

U.S. PATENT DOCUMENTS

| | | | |
|---|---|---|---|
| 2,004,001 A | 6/1935 | Henkle | |
| 3,867,728 A | 2/1975 | Stubstad et al. | |
| 4,772,287 A | 9/1988 | Ray et al. | |
| 4,904,260 A | 2/1990 | Ray et al. | |
| 5,522,899 A | 6/1996 | Michelson | |
| 5,562,738 A | 10/1996 | Boyd et al. | |
| 5,676,702 A | 10/1997 | Ratron | |
| 5,702,450 A | 12/1997 | Bisserie et al. | |
| 5,716,416 A | 2/1998 | Lin | |
| 5,893,889 A | 4/1999 | Harrington | |
| 5,928,284 A | 7/1999 | Mehdizadeh | |
| 6,086,595 A | 7/2000 | Yonemura et al. | |
| 6,156,040 A | 12/2000 | Yonemura et al. | |
| 6,179,874 B1 | 1/2001 | Cauthen | |
| 6,231,609 B1 | 5/2001 | Mehdizadeh | |
| 6,440,168 B1 | 8/2002 | Cauthen | |
| 6,468,311 B2 | 10/2002 | Boyd et al. | |
| 6,562,041 B1 | 5/2003 | Yonemura et al. | |
| 6,572,653 B1 | 6/2003 | Simonson | |

(Continued)

FOREIGN PATENT DOCUMENTS

EP 1198209 4/2002

(Continued)

*Primary Examiner* — Eduardo C Robert
*Assistant Examiner* — Christina Negrelli
(74) *Attorney, Agent, or Firm* — Nutter McClennen & Fish LLP

(57) ABSTRACT

Various exemplary instruments for introducing an implant using a posterolateral approach are also provided, as well as various exemplary methods for using such instruments. In general, the instruments are configured to interconnect to an implant and/or to a guide member such that the components are all docked relative to one another. This allows the various components of a multi-piece implant to be mated intraoperatively within the disc space, and in particular to be guided into alignment with one another.

19 Claims, 30 Drawing Sheets

U.S. PATENT DOCUMENTS

| | | |
|---|---|---|
| 6,610,093 B1 | 8/2003 | Pisharodi |
| 6,645,248 B2 | 11/2003 | Casutt |
| 6,679,915 B1 | 1/2004 | Cauthen |
| 6,692,495 B1 | 2/2004 | Zacouto et al. |
| 6,723,126 B1 | 4/2004 | Berry |
| 6,814,737 B2 | 11/2004 | Cauthen |
| 6,846,328 B2 | 1/2005 | Cauthen |
| 6,852,126 B2 | 2/2005 | Ahlgren |
| 6,881,228 B2 | 4/2005 | Zdeblick et al. |
| 6,893,465 B2 | 5/2005 | Huang et al. |
| 6,896,680 B2 | 5/2005 | Michelson |
| 6,896,701 B2 | 5/2005 | Boyd et al. |
| 7,052,515 B2 | 5/2006 | Simonson |
| 7,267,690 B2 | 9/2007 | Felt |
| 7,481,840 B2 | 1/2009 | Zucherman et al. |
| 7,591,853 B2 * | 9/2009 | Felt et al. .................... 623/17.16 |
| 2001/0032017 A1 | 10/2001 | Alfaro et al. |
| 2003/0036798 A1 | 2/2003 | Alfaro et al. |
| 2003/0055427 A1 | 3/2003 | Graf |
| 2003/0135275 A1 | 7/2003 | Garcia et al. |
| 2003/0199982 A1 | 10/2003 | Bryan |
| 2003/0220643 A1 | 11/2003 | Ferree |
| 2004/0049280 A1 | 3/2004 | Cauthen |
| 2004/0073312 A1 | 4/2004 | Eisermann et al. |
| 2004/0138749 A1 | 7/2004 | Zucherman et al. |
| 2004/0138753 A1 | 7/2004 | Ferree |
| 2004/0143270 A1 | 7/2004 | Zucherman et al. |
| 2004/0143332 A1 | 7/2004 | Krueger et al. |
| 2004/0151618 A1 | 8/2004 | Bendiner et al. |
| 2004/0153157 A1 | 8/2004 | Keller |
| 2004/0153159 A1 | 8/2004 | Cauthen |
| 2004/0158254 A1 | 8/2004 | Eisermann |
| 2004/0158328 A1 | 8/2004 | Eisermann |
| 2004/0167538 A1 | 8/2004 | Gerber et al. |
| 2004/0181284 A1 | 9/2004 | Simonson |
| 2004/0181285 A1 | 9/2004 | Simonson |
| 2004/0186577 A1 | 9/2004 | Ferree |
| 2004/0225362 A1 | 11/2004 | Richelsoph |
| 2004/0225363 A1 | 11/2004 | Richelsoph |
| 2004/0225364 A1 | 11/2004 | Richelsoph et al. |
| 2004/0225365 A1 | 11/2004 | Eisermann et al. |
| 2004/0225366 A1 | 11/2004 | Eisermann et al. |
| 2004/0254644 A1 | 12/2004 | Taylor |
| 2004/0267369 A1 | 12/2004 | Lyons et al. |
| 2005/0033431 A1 | 2/2005 | Gordon et al. |
| 2005/0033432 A1 | 2/2005 | Gordon et al. |
| 2005/0033435 A1 * | 2/2005 | Belliard et al. ............ 623/17.14 |
| 2005/0033437 A1 | 2/2005 | Bao et al. |
| 2005/0033439 A1 | 2/2005 | Gordon et al. |
| 2005/0043800 A1 | 2/2005 | Paul et al. |
| 2005/0043802 A1 | 2/2005 | Eisermann et al. |
| 2005/0049623 A1 | 3/2005 | Moore et al. |
| 2005/0065610 A1 | 3/2005 | Pisharodi |
| 2005/0085909 A1 | 4/2005 | Eisermann |
| 2005/0102027 A1 | 5/2005 | Ferree |
| 2005/0102029 A1 | 5/2005 | Blain |
| 2005/0102030 A1 | 5/2005 | Yuksel et al. |
| 2005/0107881 A1 | 5/2005 | Alleyne et al. |
| 2005/0113918 A1 | 5/2005 | Messerli et al. |
| 2005/0113925 A1 | 5/2005 | Carli |
| 2005/0113926 A1 | 5/2005 | Zucherman et al. |
| 2005/0113928 A1 | 5/2005 | Cragg et al. |
| 2005/0113929 A1 | 5/2005 | Cragg et al. |
| 2005/0119747 A1 * | 6/2005 | Fabris Monterumici et al. .......................... 623/17.11 |
| 2005/0119752 A1 | 6/2005 | Williams et al. |
| 2005/0125061 A1 | 6/2005 | Zucherman et al. |
| 2005/0125062 A1 | 6/2005 | Biedermann et al. |
| 2005/0125063 A1 | 6/2005 | Matge et al. |
| 2005/0125065 A1 | 6/2005 | Zucherman et al. |
| 2005/0130929 A1 | 6/2005 | Boyd |
| 2005/0131536 A1 | 6/2005 | Eisermann et al. |
| 2005/0131540 A1 | 6/2005 | Trieu |
| 2005/0131541 A1 | 6/2005 | Trieu |
| 2005/0131542 A1 | 6/2005 | Benzel et al. |
| 2005/0131543 A1 | 6/2005 | Benzel et al. |
| 2005/0131544 A1 | 6/2005 | Kuras et al. |
| 2005/0171610 A1 | 8/2005 | Humphreys et al. |
| 2006/0293752 A1 | 12/2006 | Moumene et al. |
| 2007/0299521 A1 | 12/2007 | Glenn et al. |

FOREIGN PATENT DOCUMENTS

| | | |
|---|---|---|
| EP | 1527759 | 5/2005 |
| EP | 1531765 A2 | 5/2005 |
| EP | 1532948 | 5/2005 |
| EP | 1534193 A1 | 6/2005 |
| EP | 1534194 A2 | 6/2005 |
| EP | 1539051 A1 | 6/2005 |
| EP | 1539052 A1 | 6/2005 |
| WO | WO-9909896 | 3/1999 |
| WO | WO-03071992 | 9/2003 |
| WO | WO-2004002291 | 1/2004 |
| WO | WO-2004016205 | 2/2004 |
| WO | WO-2004016217 | 2/2004 |
| WO | WO-2004019828 | 3/2004 |
| WO | WO-2004019830 | 3/2004 |
| WO | WO-2004026186 | 4/2004 |
| WO | WO-2004098465 | 11/2004 |
| WO | WO-2004098466 | 11/2004 |
| WO | WO-2005011522 | 2/2005 |
| WO | WO-2005013862 | 2/2005 |
| WO | WO-2005037028 | 4/2005 |
| WO | WO-2005037148 | 4/2005 |
| WO | WO-2005039455 | 5/2005 |
| WO | WO-2005041793 | 5/2005 |
| WO | WO-2005041818 | 5/2005 |
| WO | WO-2005046534 | 5/2005 |
| WO | WO-2005051228 | 6/2005 |
| WO | WO-2005051243 | 6/2005 |
| WO | WO-2005051246 | 6/2005 |
| WO | WO-2005053579 | 6/2005 |
| WO | WO-2005053580 | 6/2005 |

* cited by examiner

METHODS AND INSTRUMENTATION FOR DISC REPLACEMENT

CROSS REFERENCE TO RELATED APPLICATIONS

The present application claims priority to U.S. Provisional Application No. 60/807,397 filed on Jul. 14, 2006. The present application is also a continuation-in-part of U.S. patent application Ser. No. 11/277,725 filed on Mar. 28, 2006 and entitled "Artificial Disc Replacement Using Posterior Approach," and U.S. patent Ser. No. 11/277,726 filed on Mar. 28, 2006 and entitled "Artificial Disc Replacement Using Posterior Approach," which are hereby incorporated by reference in their entireties.

FIELD OF THE INVENTION

The present application relates to methods and devices for spinal surgery, and in particular for posterior disc replacement.

BACKGROUND OF THE INVENTION

Advancing age, as well as injuries, can lead to changes in the various bones, discs, joints and ligaments of the body. In particular, these changes can manifest themselves in the form of damage or degeneration of an intervertebral disc, the result of which is mild to severe chronic back pain. Intervertebral discs serve as "shock" absorbers for the spinal column, absorbing pressure delivered to the spinal column. Additionally, they maintain the proper anatomical separation between two adjacent vertebra. This separation is necessary for allowing both the afferent and efferent nerves to exit and enter, respectively, the spinal column.

Treatment for a diseased or damaged disc can involve the removal of the affected disc and subsequent fusion of the opposing vertebra to one another. Spinal fusion consists of fusing the adjacent vertebrae through the disc space (the space previously occupied by the spinal disc interposed between the adjacent vertebral bodies). Typically, a fusion cage and/or bone graft is placed into the disc space to position the vertebrae apart so as to create more space for the nerves, to restore the angular relationship between the adjacent vertebrae to be fused, and to provide for material that can participate in and promote the fusion process.

More recently, artificial disc replacements have been developed that allow one or more degrees of freedom between the adjacent vertebrae, thereby restoring function to the vertebrae. Surgical procedures for replacing intervertebral disc material, rather than fusing of the vertebrae, have included both anterior approaches and posterior approaches to the spinal column. The anterior approach to the spinal column is complicated by the internal organs that must be bypassed or circumvented to access the vertebrae. The posterior approach (from the back of the patient) encounters the spinous process, superior articular process, and the inferior articular process. These features may be removed to ease insertion of the artificial disc replacement into the intervertebral space, as the disc replacement must have a height sufficient to restore normal height to the adjacent vertebrae, and it must have a depth and width, or surface area, that is sufficient to ensure contact with the peripheral bone, e.g., cortical bone, surrounding the vertebral endplates.

Accordingly, there remains a need for improved methods and devices for replacing a disc.

SUMMARY OF THE INVENTION

The present invention provides various methods and devices for replacing a disc. In one embodiment, an artificial disc replacement implant is provided and includes a central component having a superior member adapted to be positioned adjacent to an endplate of a superior vertebra, and an inferior member adapted to be positioned adjacent to an endplate of an adjacent inferior vertebra. The superior and inferior members can be movable relative to one another. The central component can also include leading and trailing ends and opposed first and second lateral sides extending between the leading and trailing ends. At least one of the lateral sides can include a mating element formed thereon. The implant can also include at least one lateral component having a mating element removably matable to the mating element on at least one of the first and second lateral sides of the central component. The central component and the lateral component(s) can also have a superior and inferior footprint, when mated, that is substantially equal to a superior and inferior footprint of superior and inferior vertebrae between which the implant is adapted to be positioned.

While the central component can have a variety of configurations, in one embodiment the superior and inferior members each include a bone-contacting surface adapted to be positioned adjacent to bone, and an opposed articulating surface. The articulating surfaces can be configured to move relative to one another to allow movement between the superior and inferior members. For example, the articulating surface on one of the superior and inferior members can include a concave cavity formed therein, and the articulating surface on the other one of the superior and inferior members can include a convex protrusion formed thereon and adapted to be received within the concave cavity.

The lateral component(s) can also have a variety of configurations. For example, the lateral component(s) can be substantially U-shaped such that the lateral component(s) is elastic. In another embodiment, the lateral component(s) can include a superior lateral member removably matable to the superior member of the central component, and inferior lateral member removably matable to the inferior member of the central component. The superior and inferior lateral members can be mated to one another by a compressible or elastic element, such as an elastomer, extending therebetween. In another embodiment, the lateral component(s) can include a first lateral component having a superior lateral member and an inferior lateral member, and a second lateral component having a superior lateral member and an inferior lateral member. The first lateral component can be removably matable to the first lateral side of the central component, and the second lateral component can be removably matable to the second lateral side of the central component.

The implant can also include other features, such as one or more surface protrusions formed on at least one of the superior and inferior members. In one embodiment, the superior and inferior members can each include a keel extending between the leading and trailing ends. In an exemplary embodiment, the keel has a height that increase in from the leading end to the trailing end, and the keel extends substantially parallel to the opposed lateral sides. In other embodiment, the implant can include one or more markers, such as a cut-out, radiolucent or radiopaque marker, or other feature formed on the superior and/or inferior members to facilitate positioning of the members.

In another embodiment, an artificial disc replacement implant is provided for insertion within a disc space formed between adjacent vertebral bodies. The implant can include a central component including superior and inferior members movable relative to one another, and having a superior surface adapted to be positioned adjacent to a superior endplate of a superior vertebra, and an inferior surface adapted to be positioned adjacent to an inferior endplate of an inferior vertebra. The central component can also include opposed leading and trailing ends and opposed lateral sides extending between the leading and trailing ends. A maximum width extending between the opposed lateral sides can be less than a width of a posterolateral surgical access window extending into a disc space into which said central component is adapted to be inserted, and a length extending between the leading and trailing ends can be sufficient to allow the leading and trailing ends to contact peripheral bone that surrounds the superior and inferior endplates which the central component is adapted to be positioned between. The central component can also include a surface area on each of the superior and inferior surfaces that is smaller than a surface area of the superior and inferior endplates which the central component is adapted to be positioned between. In certain exemplary embodiments, the central component can be in the shape of a parallelogram. The implant can also include at least one lateral component removably matable to a lateral side of the central component. For example, the implant can include a superior lateral member adapted to mate to the superior member of the central component, and an inferior lateral member adapted to mate to the inferior member of the central component.

A method for implanting a disc replacement is also provided and can include inserting a central component along an axis extending in a posterior-lateral direction into a disc space formed between adjacent vertebrae, and inserting at least one lateral component along an axis extending in a posterior-anterior or a posterolateral direction into the disc space to couple the lateral component to the central component. Prior to inserting the central component, a surgical access window that extends from an incision formed in a patient's skin at a location posterior-lateral to the patient's spinal column to a disc space is preferably formed between adjacent superior and inferior vertebrae, and a disc disposed within the disc space is removed. The access window can be formed by removing a facet joint extending between the adjacent superior and inferior vertebrae. The adjacent superior and inferior vertebrae can also be distracted from a contra-lateral or ipsilateral side prior to inserting the central component. Various techniques can also be used to insert the lateral component(s), and in one embodiment a first lateral component can be inserted along a first axis extending in a generally posterior-anterior direction into the disc space to couple the first lateral component to a first lateral side of the central component, and a second first lateral component can be inserted along a second axis extending in a generally posterior-anterior direction into the disc space to couple the second lateral component to a second, opposed lateral side of the central component. In other embodiments, the central component can include at least one protrusion, such as a keel, formed on at least one of a superior and inferior surface thereof, and the keel can be aligned with the axis of the surgical access window. A marker, such as a cut-out, can be formed in the keel, and the method can include imaging the cut-out to determine a position of the central component relative to the adjacent superior and inferior vertebrae.

In another embodiment, a method for implanting an artificial disc replacement is provided and includes inserting a central component along a posterolateral axis of a surgical access window extending posterolaterally into a disc space between adjacent superior and inferior vertebrae. The central component can have a width that is less than a width of the surgical access window, and a superior member that is positioned adjacent to a superior endplate of the superior vertebra and an inferior member that is positioned adjacent to an inferior endplate of the inferior vertebra. The superior and inferior members can maintain the adjacent superior and inferior vertebrae at a distance apart from one another, and they can be movable relative to one another to allow movement between the adjacent superior and inferior vertebrae. In an exemplary embodiment, the central component includes a leading end and a trailing end, and the leading and trailing ends of the central component are positioned in contact with peripheral bone surrounding the superior and inferior endplates. The method can further include rotating one of the superior and inferior members relative to the other one of the superior and inferior members to position the rotated member along a contra-lateral axis.

In another embodiment, a method for implanting an artificial disc replacement is provided and includes inserting a superior member along a first posterolateral axis of a first surgical access window extending posterolaterally into a disc space between adjacent superior and inferior vertebrae. The superior member can have a width that is equal to or less than a width of the first surgical access window. The method further includes inserting an inferior member along a second posterolateral axis of a second surgical access window extending posterolaterally into a disc space between adjacent superior and inferior vertebrae. The second posterolateral axis can be located on the contralateral side of the vertebra from the first posterolateral axis, and the inferior member can have a width that is equal to or less than a width of the second surgical access window. The superior member is positioned adjacent an endplate of the superior vertebra, and the inferior member is positioned adjacent an endplate of the inferior vertebra such that the superior and inferior members maintain the adjacent superior and inferior vertebrae at a distance apart from one another.

In yet another embodiment, a method for implanting a spinal implant is provided and includes manipulating a first inserter tool to position a first component of a spinal disc implant within a disc space between adjacent vertebrae, and advancing a second inserter tool along a guide that is coupled to at least one of the first inserter tool and the first component such that a second component mated to the second inserter tool is guided into mating alignment with the first component to thereby mate the second component to the first component. In an exemplary embodiment, the first inserter tool is inserted into the disc space on a posterolateral side of the disc space, and the second inserter tool is inserted into the disc space on a contralateral side of the disc space. The method can also include advancing a third inserter tool along the guide such that a third component mated to the third inserter tool is guided into mating alignment with the first component to thereby mate the third component to the first component. In an exemplary embodiment, the second component is mated to a lateral side of the first component, and the third component is mated to a contralateral side of the first component.

The guide can have a variety of configurations. For example, the guide can be a guidewire that is coupled to the first inserter tool, the first component, and the second inserter tool, and the second inserter tool can be slid along the guidewire. In another embodiment, the guide can be a frame coupled to the first inserter tool, and the second inserter tool can be is advanced through an opening in the frame. In certain aspects, the frame can be positioned at least partially outside of the disc space.

In other aspects, a method for implanting an artificial disc replacement is provided and includes inserting a central inserter tool into a disc space between adjacent vertebrae to position a central component mated to the central inserter tool within the disc space, and inserting a first lateral inserter tool into the disc space to mate a first lateral component mated to the first lateral inserter tool to a first lateral side of the central component. The method can also include, prior to inserting the first lateral inserter tool into the disc space, positioning a retaining tool against the central component to maintain the central component in a substantially fixed position and detaching and removing the central inserter tool from the central component. In one embodiment, the central inserter tool can be inserted into the disc space on a posterolateral side of the disc space, and the first lateral inserter can be inserted into the disc space on a contralateral side of the disc space. The central inserter tool can optionally be used to maintain the central component in a substantially fixed position while the first lateral component is mated to the central component.

In another embodiment, the method can include advancing the first lateral inserter tool along a guide coupled to at least one of the central component and the central inserter tool. The guide can be, for example, a guidewire mated to the central inserter tool and the central component. Inserting the first lateral inserter tool into the disc space can thus include coupling the guidewire mated to the first lateral inserter tool, and advancing the first lateral inserter tool along the guidewire to mate the first lateral component to the central component. In one embodiment, prior to inserting the central inserter tool into a disc space, the guidewire can be introduced into the disc space using a guidewire inserter, and a terminal end of the guidewire located in the disc space can be grasped with a grasper to pull the terminal end of the guidewire out of the disc space such that the guide wire has first and second terminal ends that are positioned outside of the disc space and a unshaped portion that is positioned in the disc space. In another embodiment, the guide can be a frame mated to the central inserter tool, and inserting the first lateral inserter tool into the disc space can include inserting the first lateral inserter tool through an opening formed in the frame such that the frame guides the first lateral component into mating alignment with the central component. The method can also include inserting a second lateral inserter tool into the disc space to mate a second lateral component mated to the second lateral inserter tool to a contralateral side of the central component. In an exemplary embodiment, the central inserter tool is mated to the contralateral side of the central component, and, prior to inserting the second lateral inserter tool into the disc space, the central inserter tool is disengaged from the contralateral side of the central component to allow the second lateral component to be mated to the contralateral side of the central component.

A spinal implant and instrumentation system is also provided, and in one embodiment the system can include an implant configured to be positioned within a disc space between adjacent vertebrae and having a central component and a first lateral component that is removably matable to a first lateral side of the central component, a central inserter tool configured to removably mate to the central component, a first lateral inserter tool configured to removably mate to the first lateral component, and a guide configured to removably interconnect the implant, the central inserter tool, and the first lateral inserter tool to allow the first lateral component to be intraoperatively guided into alignment with and mated to the first lateral side of the central component.

In one embodiment, the guide can be a guidewire configured to removably mate to the central inserter tool and the central component, and configured to slidably receive the first lateral inserter tool to guide the first lateral component into mating alignment with the central component. The central inserter tool and the first lateral inserter tool can include a guidewire channel formed therein and configured to receive the guidewire.

In another embodiment, the guide can be a frame configured to removably mate to the central inserter tool and to slidably receive the first lateral inserter tool. The frame can include a first channel adapted to removably receive the central inserter tool, and a second channel adapted to removably receive the first lateral inserter tool. The first and second channels can be positioned so as to align the central inserter tool with a first lateral side of a disc space and the lateral inserter tool with a contralateral side of the disc space. The frame can also include a third channel and the system can include a second lateral inserter tool configured to removably mate a second lateral component to the central component. The second and third channels in the frame can be positioned so as to align the first lateral inserter tool and a second lateral inserter tool with first and second opposed lateral sides of the central component.

In other aspects, the implant can include a second lateral component that is removably matable to a second lateral side of the central component, and the system can further include a second lateral inserter tool configured to removably mate to the second lateral component. The central inserter tool can also be removably matable to the second lateral side of the central component.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for replacing a spinal disc. In an exemplary embodiment, artificial disc replacements and methods are provided wherein at least a portion of a disc replacement can be implanted using a posterolateral approach. The posterolateral annulus, and posterior lip of the vertebral bodies may be removed to access the disc space, leaving the remaining annulus and the anterior and posterior longitudinal ligaments in tact. A portion or all of the facet joints may be removed to provide better access to the disc space. The posterolateral pathway is referred to herein as a posterolateral surgical access window. A typical posterolateral access window has a maximum width of about 13 mm without displacing nerves or dural elements and a maximum height of about 11 mm without distraction. The present invention provides disc implants which can be at least partially introduced using a posterolateral approach, yet that have a size that is sufficient to restore height to the adjacent vertebrae, and that is sufficient to maximize contact with the endplates of the adjacent vertebrae.

Figure 1A:
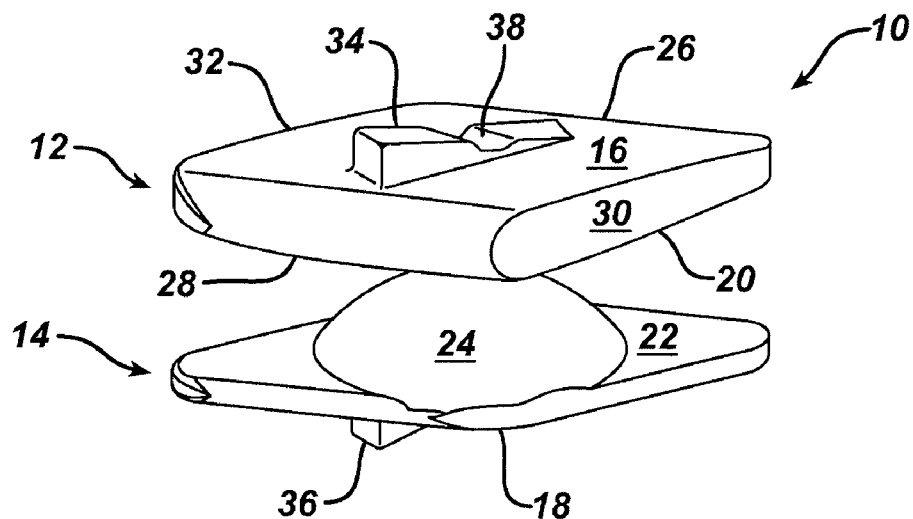
FIG. 1A is a side perspective view of one exemplary embodiment of an implant that can be introduced between adjacent vertebrae using a posterolateral approach.
Figure 1B:
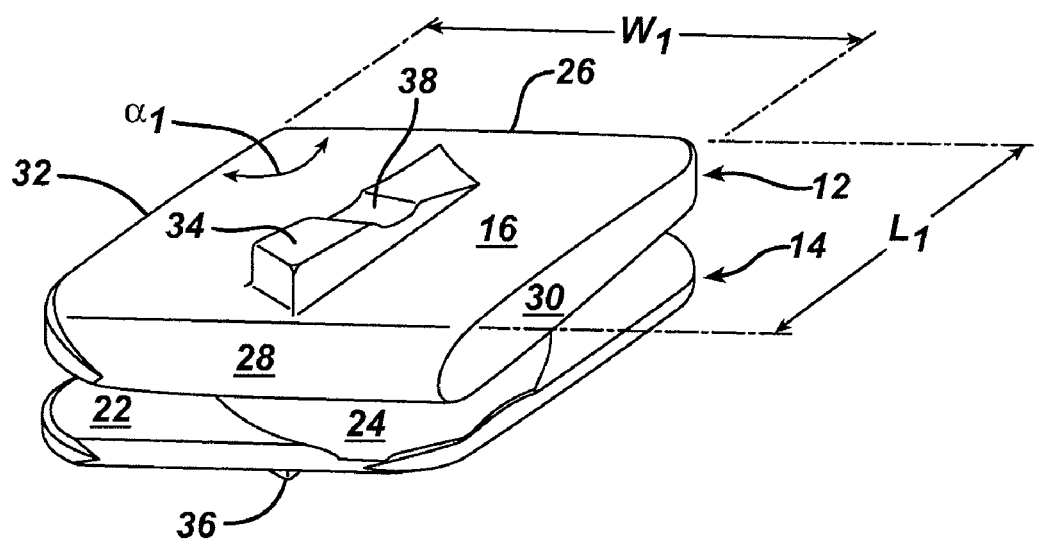
FIG. 1B is a top perspective view of the implant shown in FIG. 1A.

FIGS. 1A and 1B illustrate one exemplary embodiment of an implant that can be introduced through a posterolateral surgical access window. As shown, the implant 10 generally includes a superior member 12 adapted to be positioned adjacent to an endplate of a superior vertebra, and an inferior member 14 adapted to be positioned adjacent to an endplate of an inferior vertebra. In particular, each member 12, 14 includes a bone-contacting surface 16, 18 configured to be positioned adjacent to an endplate of a vertebra, and an opposed mating or articulating surface 20, 22 configured to be positioned adjacent to one another. Together, the superior and inferior members 12, 14 are configured to restore height to the adjacent vertebrae, and they can optionally move relative to one another to restore motion to the adjacent vertebrae. While various techniques can be used to allow the superior and inferior members 12, 14 to move relative to one another, in one exemplary embodiment the mating surfaces 20, 22 on the superior and inferior members 12, 14 are articulating surfaces. For example, at least one of the members, e.g., the superior member 12, can include a concave recess formed therein, and the other member, e.g., the inferior member 14, can include a convex or spherical member 24 formed thereon. The spherical member 24 can be movably disposed within the concave recess to allow movement between the superior and inferior members 12, 14, thereby allowing movement between the vertebrae.

Figure 1C:
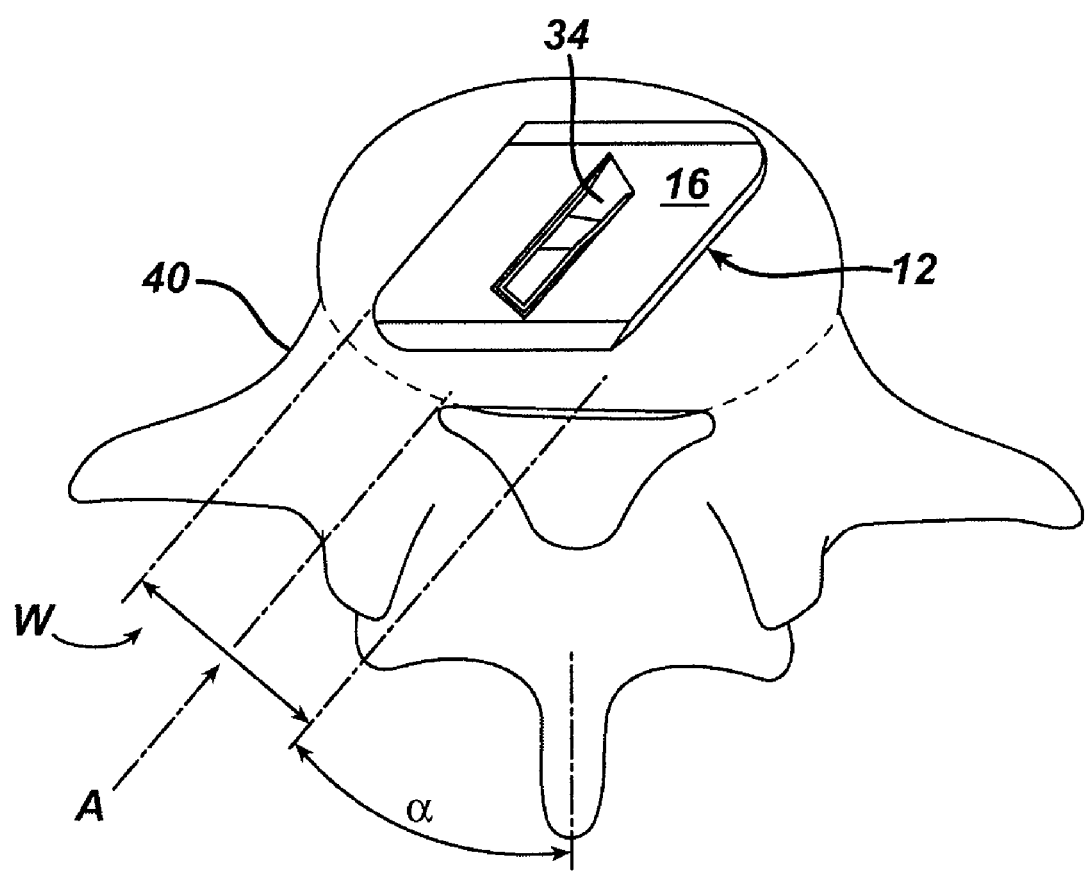
FIG. 1C is a top view of the implant shown in FIGS. 1A-1B positioned on a vertebral body, showing a posterolateral surgical access window for introducing the implant.

As explained above, the implant 10 can have a configuration that allows the implant 10 to be introduced through a posterolateral approach surgical access window, yet that restores height to the adjacent vertebrae and maximizes contact with the endplates. As shown in FIGS. 1A and 1B, the implant 10 includes opposed leading and trailing ends 26, 28 and opposed lateral sides 30, 32 extending between the leading and trailing ends 26, 28. The width $w_1$ extending between the opposed lateral sides 30, 32 can be equal to or less than a width of a posterolateral access window into which the implant 10 is adapted to be inserted, and in an exemplary embodiment the width $w_1$ is less than about 20 mm. The length $L_1$ of the implant 10 extending between the leading and trailing ends 26, 28 can also vary, but in certain exemplary embodiments the length $L_1$ is sufficient to allow the leading and trailing ends 26, 28 of the implant 10 to contact peripheral bone, e.g., cortical bone, surrounding the superior and inferior endplate, and in particular to contact the cortical bone or both the posterior and anterior sides of the disc space. By way of non-limiting example, the length $L_1$ can be in the range of about 25 mm to 30 mm. As a result of the length $L_1$ and width $w_1$ of the implant 10, the surface area on each of the superior and inferior surfaces of the implant 10 is smaller than a surface area of the superior and inferior endplates which the implant 10 is adapted to be positioned between. The particular shape of the implant, however, is preferably maximized to maximize the surface area and to occupy the space defined by a posterolateral axis window. As shown in FIG. 1C, the access window extends in a posterolateral direction at an angle of about 40° from the axis of the spinous process, and the access window has a width of about 20 mm. The illustrated implant 10 has a shape in the form of a parallelogram with the opposed lateral sides 30, 32 extending at an angle $\alpha_1$ that is greater than 90° relative to the leading and trailing edges 26, 28. This will allow the implant 10 to be introduced through and along an axis A of a posterolateral access window W, as shown in FIG. 1C, and to be positioned diagonally across the endplates of the adjacent vertebrae. The shape of the implant 10 will also allow the implant to occupy the entire space defined by the access window, thereby maximizing the size of the implant and thus the surface contact between the implant and the endplates of the adjacent vertebrae.

The implant 10 can also include other features to facilitate use of the device. For example, as shown in FIGS. 1A-1C the superior and/or inferior members 12, 14 can include a protrusion, such as a keel 34, 36, formed on the bone-contacting surfaces 16, 18 thereon to facilitate insertion of the device. Each keel 34, 36 preferably extends in a posterolateral direction, substantially parallel to the lateral sides of the implant 10, such that it can be used to guide the implant 10 along the axis A of the access window W. The implant 10 can also include one or more features, such as a marker, to confirm the proper position of the implant 10 once it is implanted. For example, as shown in FIGS. 1A-1C, the keel 34 includes a cut-out 38 formed therein. The cut-out 38 can be viewed on an image, such as an X-ray image, to ensure that the implant 10 is properly positioned within the disc space. In other embodiments, the marker can be a radiopaque or radiolucent marker formed on the implant. A person skilled in the art will appreciate that a variety of other techniques can be used to facilitate insertion and/or alignment of the implant 10, and that the implant can include a variety of other features.

Figure 2A:
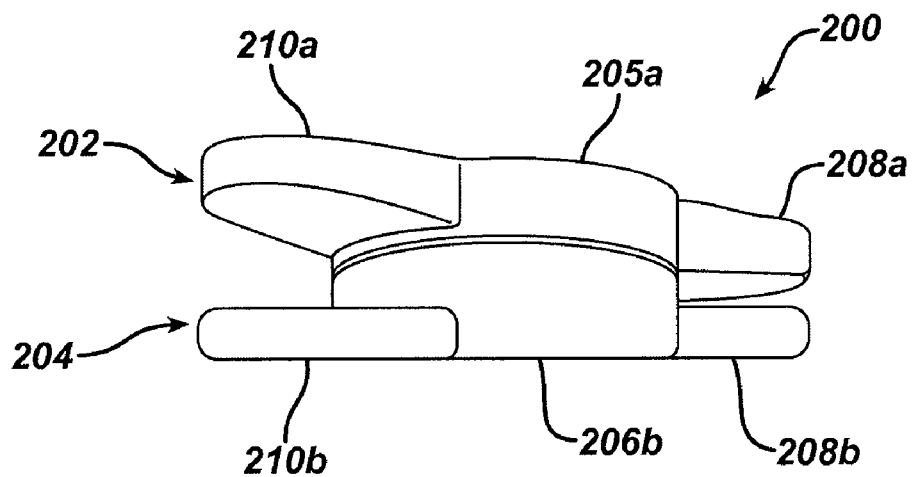
FIG. 2A is a side perspective view of another embodiment of an implant that can be introduced between adjacent vertebrae using a posterolateral approach.
Figure 2B:
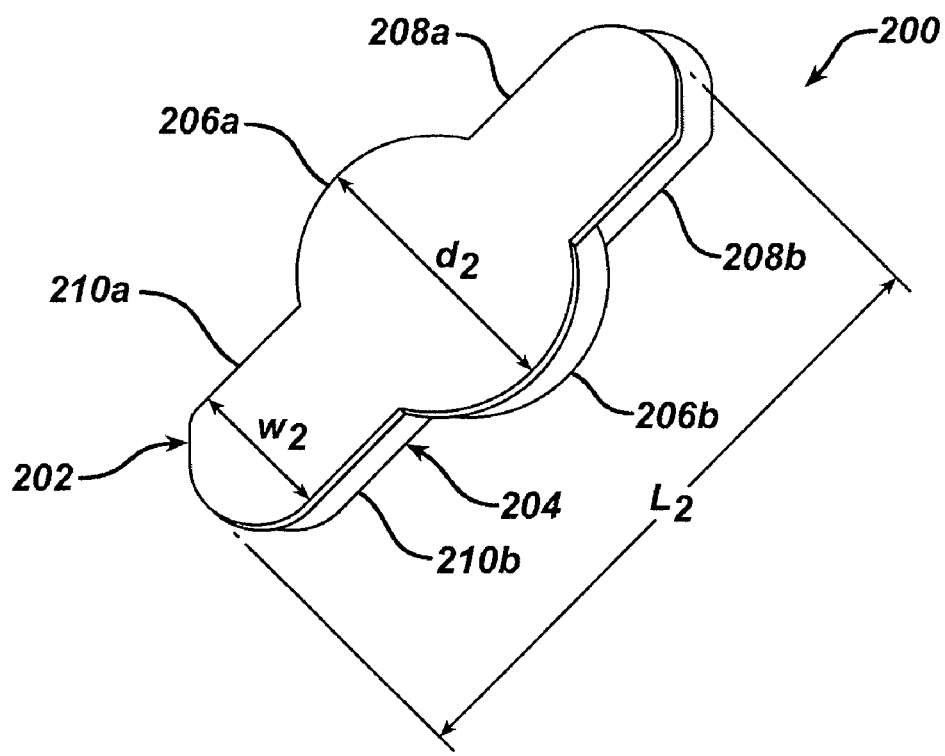
FIG. 2B is a top perspective view of the implant shown in FIG. 2A.
Figure 2C:
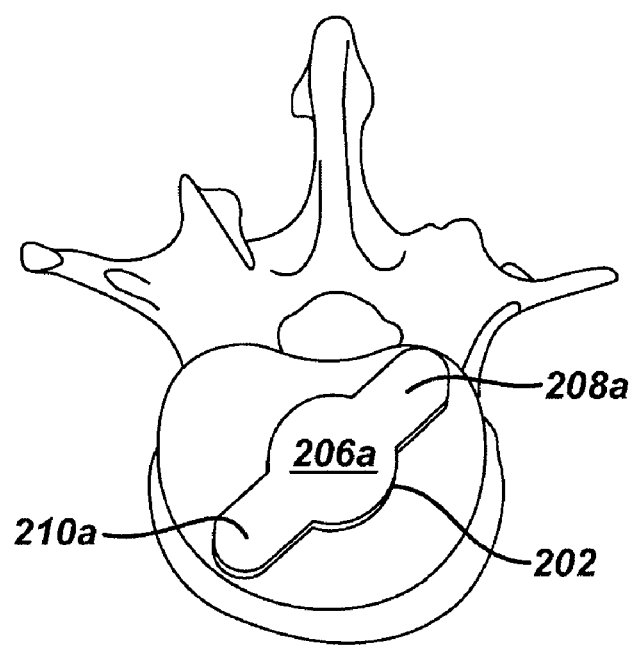
FIG. 2C is a top view of the implant shown in FIGS. 2A-2B positioned on a vertebral body.

As indicated above, the implant can have a variety of other shapes and sizes to allow the implant to be introduced through a posterolateral access window. FIGS. 2A-2C illustrate another embodiment of an implant 200 which generally includes superior and inferior members 202, 204 similar to those described with respect to FIGS. 1A-1B. In particular, the superior and inferior members 202, 204 are adapted to be positioned between adjacent vertebrae, and they are movable relative to one another to allow movement of the adjacent vertebrae. In this embodiment, however, each member 202, 204 of the implant 200 has an elongate shape with a central portion 206a, 206b having opposed leading and trailing extensions 208a, 208b, 210a, 210b. Each central portion 206a, 206b can have a circular shape with a diameter $d_2$ that is greater than a width $w_2$ of the opposed leading and trailing extensions 208a, 208b, 210a, 210b, but that is less than or equal to a width of a posterolateral access window. The circular shape of the central portion 206a, 206b can allow the central portions 206a, 206b to articulate relative to one another. For example, concave and convex surfaces can be formed on the articulating surface of each member 202, 204 to allow movement therebetween. The implant can also have a length $L_2$ that varies, but in an exemplary embodiment the length $L_2$ is preferably sufficient to allow the leading and trailing extensions 208a, 208b, 210a, 210b to contact cortical bone surrounding the superior and inferior endplates.

Figure 2D:
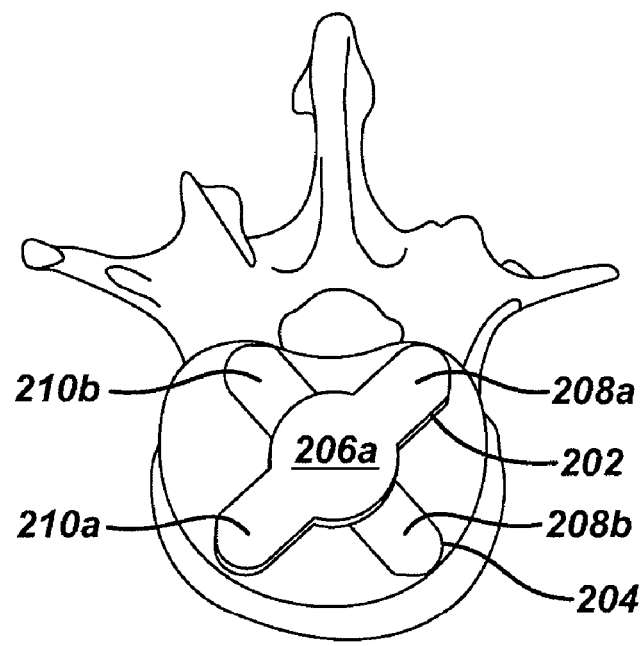
FIG. 2D is a top view of the implant shown in FIG. 2C having one of the superior and inferior members of the implant rotated about 90°.

In use, as shown in FIG. 2C, the diameter $d_2$ of the central portions 206a, 206b and the width $w_2$ of the extensions 208a, 208b, 210a, 210b of the implant 200 allow the implant 200 to be introduced through the posterolateral surgical access window, i.e., diagonally into the disc space. The length $L_2$ allows the leading and trailing extensions 208a, 208b, 210a, 210b of the implant 200 to contact the cortical bone adjacent to the posterior and anterior sides of the vertebrae, as shown. In order to further increase stability of the implant, one of the superior and inferior members 202, 204 can be rotated relative to the other member. FIG. 2D illustrates the members 202, 204 rotated 90° relative to one another. This configuration allows the implant 200 to contact cortical bone at four locations, two on each of the posterior and anterior sides of the disc space, resulting in increased stability of the implant 200. A person skilled in the art will appreciate that members 202, 204 can be rotated at any angle relative to one another to increase contact with the endplates of adjacent bone, or the superior and inferior members 202, 204 can remain in alignment with one another. In other embodiments, the members 202, 204 can be introduced through separate windows formed on a contralateral sides of the vertebra to position the members as shown in FIG. 2D.

In other embodiments, an artificial disc implant can include a central component and one or more lateral components that mate to the central component. The central component can be similar to the implants previously described above, or it can have various other configurations, but it is preferably configured to be introduced through a posterolateral surgical access window. The lateral component(s) are configured to mate to the lateral side(s) of the central component to maximize contact between the implant and the endplates of the adjacent vertebrae. In an exemplary embodiment, the lateral components are configured to be introduced using a posterior approach, however virtually any technique known in the art can be used for implanting and mating the lateral component(s) to the central component.

Figure 3A:
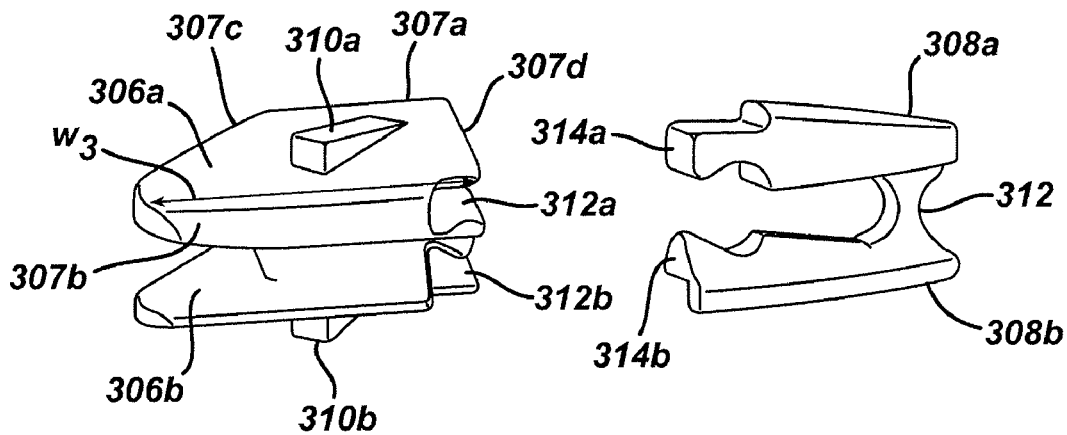
FIG. 3A is an exploded perspective view of another exemplary embodiment of an implant having a central component that can be introduced between adjacent vertebrae using a posterolateral approach and a lateral component that can mate to the central component.
Figure 3B:
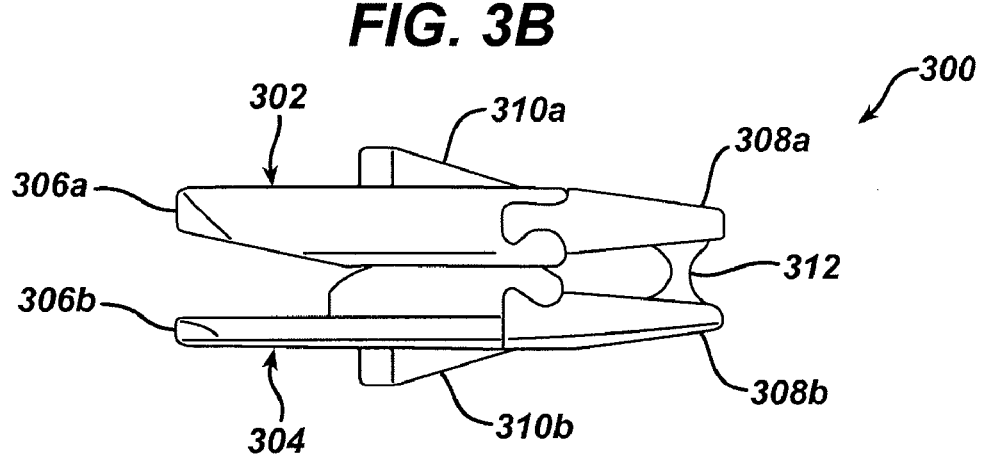
FIG. 3B is a side view of the implant shown in FIG. 3A in an assembled configuration.
Figure 3C:
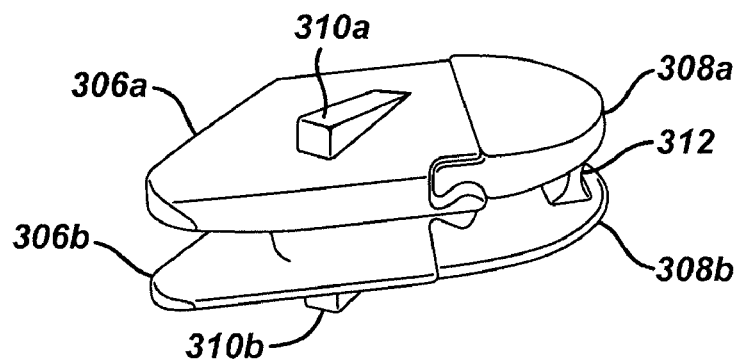
FIG. 3C is a top perspective view of the implant shown in FIG. 3A in an assembled configuration.

FIGS. 3A-3C illustrate one exemplary embodiment of an implant having a central component and a lateral component that mates to a lateral side of the central component. The configuration of the central component can vary, and it can include a single member or superior and inferior members 306a, 306b, as shown. The superior and inferior members 306a, 306b can be similar to members 12 and 14 previously described with respect to FIGS. 1A-1B, and in particular the members 306a, 306b can include opposed leading and trailing ends 307a, 307b and opposed lateral sides 307c, 307d extending therebetween. The members 306a, 306b can also be configured to move relative to one another to allow movement of the adjacent vertebrae. This can be achieved using, for example, concave and convex articulating surfaces. The superior and inferior central members 306a, 306b also preferably have a shape and size that allows the members to be introduced through a posterolateral access window. In the illustrated embodiment, each central member 306a, 306b has a shape in the form of a trapezoid, with non-parallel opposed lateral sides. A first lateral side 307c extends between the leading and trailing ends 307a, 307b at an angle that is less than or greater than 90° relative to the leading and trailing ends 307a, 307b. A second lateral side 307d extends perpendicularly between the leading and trailing ends 307a, 307b. The size can also vary, however in an exemplary embodiment the maximum width $W_3$ extending between the opposed lateral sides 307c, 307d can be equal to or less than a width of a posterolateral access window into which the central members 306a, 306b are adapted to be inserted, and the length $L_3$ extending between the leading and trailing ends 307a, 307b can be sufficient to allow the leading and trailing ends 307a, 307b of each central member 306a, 306b to contact cortical bone surrounding the disc space into which the implant 300 is inserted. As further shown, one of the lateral sides, e.g., the second lateral side 307d, of each of the superior and inferior central members 306a, 306b can include a mating element configured to mate with the lateral component. While the mating element can vary, in the illustrated embodiment a slot or groove 312a, 312b is formed in and extends along at least a portion of the straight lateral side 307a of each of the superior and inferior central members 306a, 306b. The grooves 312a, 312b are configured to receive complementary protrusions or tongues formed on the lateral component, as will be discussed below.

The lateral component can also include superior and inferior members 308a, 308b. The members 308a, 308b can vary in size and shape, but they are preferably configured to increase contact between the implant 300 and the endplates of the adjacent vertebrae. In the illustrated embodiment, each lateral member 308a, 308b has a semi-circular shape with a substantially straight edge and a curved portion extending between the ends of the straight edge. The straight edge of each lateral member 308a, 308b includes a mating element that is adapted to allow each lateral member 308a, 308b to mate to a mating component disposed on or formed within the second lateral side of each central member 306a, 306b. As shown in FIGS. 3A-3C, each lateral member 308a, 308b includes a tongue 314a, 314b extending substantially along the length of the straight edge thereof. The tongues 314a, 314b can be slidably disposed within the grooves 312a, 312b formed in the central members 306a, 306b to mate the superior and inferior lateral members 308a, 308b to the central members 306a, 306b. When mated, the central members 306a, 306b and the lateral members 308a, 308b can from an implant that has a surface area that is greater than at least 50% of a surface area of a vertebral endplate to maximum contact with the endplates, and more preferably that is greater than about 75% of a surface area of a vertebral endplate.

A person skilled in the art will appreciate that a variety of other mating techniques can be used to mate the central members 306a, 306b and the lateral members 308a, 308b of the implant 300, such as a dovetail connection, a pin-and-bore arrangement, etc. The mating connection can also include a stop that is adapted to prevent the lateral members 308a, 308b from sliding past the leading end of the central members 306a, 306b. When mated, this positions the leading and trailing edges of the lateral members 308a, 308b substantially flush with the leading and trailing edges of the central members 306a, 306b, as shown in FIGS. 3B-3C. While various techniques can be used to form a stop, in one embodiment a terminal end surface (not shown) can be formed within each groove 312a, 312b adjacent to the leading end of each central member 306a, 306b. As a result, the tongue 314a, 314b on each of the superior and inferior lateral members 308a, 308b will abut the end surface.

The implant 300 can include other features to facilitate use of the device, such as bone-engaging surface features, one or more keels 310a, 310b formed on the bone-contacting surfaces of the implant 300, or other elements to facilitate use and positioning of the implant. FIGS. 3A-3C illustrates keels similar to those previously described above in relation to FIGS. 1A-1C. FIGS. 3A-3C also illustrate a strut 312 extending between the superior and inferior lateral members 308a, 308b, which will be discussed in more detail below.

Figure 3D:
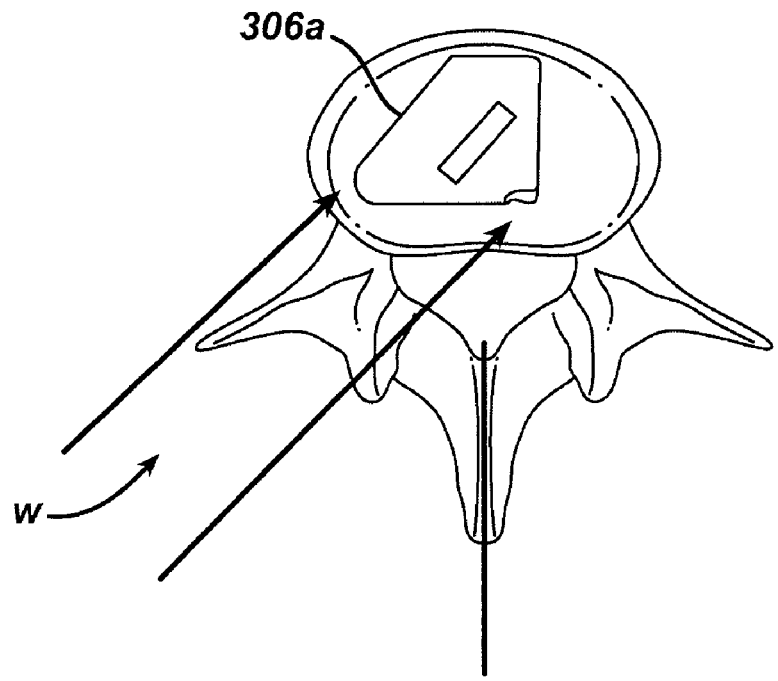
FIG. 3D is a top view of a central portion of the implant of FIGS. 3A-3C positioned on a vertebral body, showing a posterolateral surgical access window for introducing the central portion.
Figure 3E:
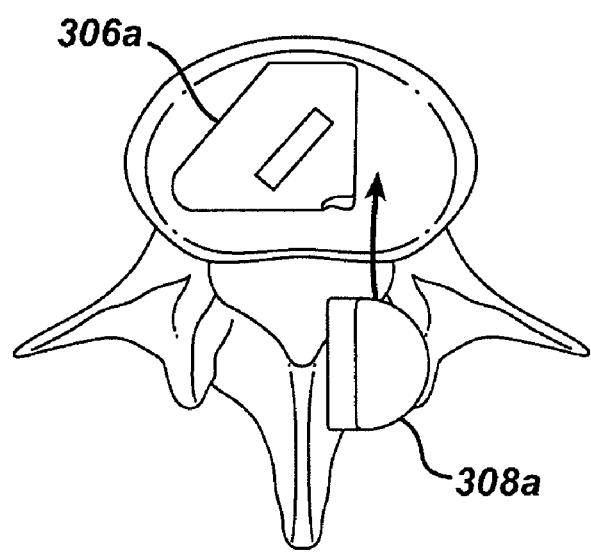
FIG. 3E is a top view of the central portion of the implant of FIG. 3D positioned on a vertebral body, showing a lateral component about to be introduced using a posterior approach to mate to the central component.

In use, as shown in FIGS. 3D and 3E, the central members 306a, 306b of the implant 300 can be introduced through the posterolateral surgical access window w to position the implant within the disc space. As shown, the shape and size of the central component occupies the space defined by the posterolateral access window, except for a region near the lateral side 307d of the implant which mates to the lateral component. The implant also has a length that allows the leading and trailing ends of the central members 306a, 306b to contact the cortical bone adjacent to the posterior and anterior sides of the vertebrae. In order to further maximize contact with the endplates of the adjacent vertebrae, the lateral members 308a, 308b can be introduced using, for example, a posterior approach, as shown in FIG. 3E. As the lateral members 308a, 308b are introduced into the disc space, the lateral members 308a, 308b can be mated to the central members 306a, 306b by sliding the complementary tongues 314a, 314b into the grooves 312a, 312b of the central members 306a, 306b.

Figure 4A:
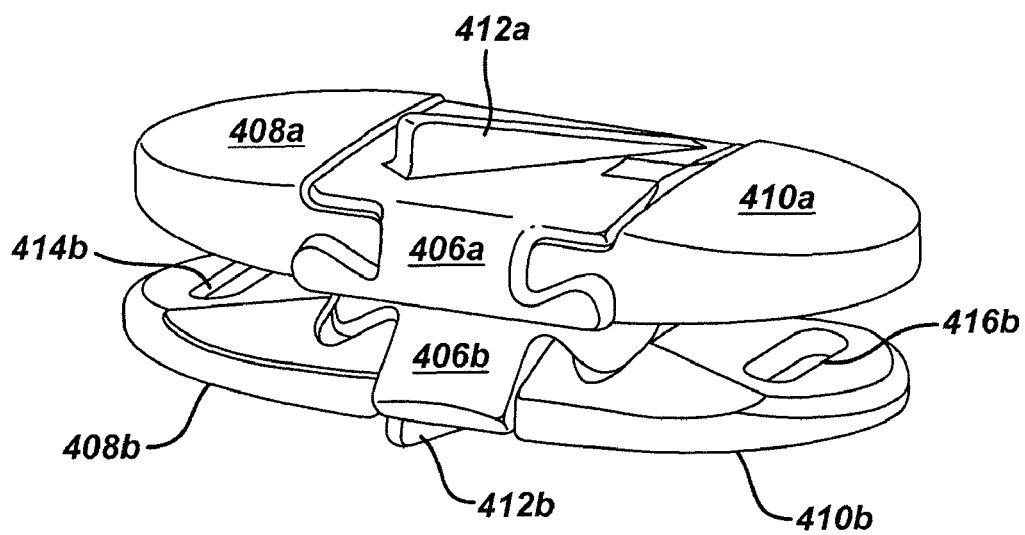
FIG. 4A is a perspective view of another exemplary embodiment of an implant having a central component that can introduced between adjacent vertebrae using a posterolateral approach and opposed lateral components that can mate to the central component.
Figure 4B:
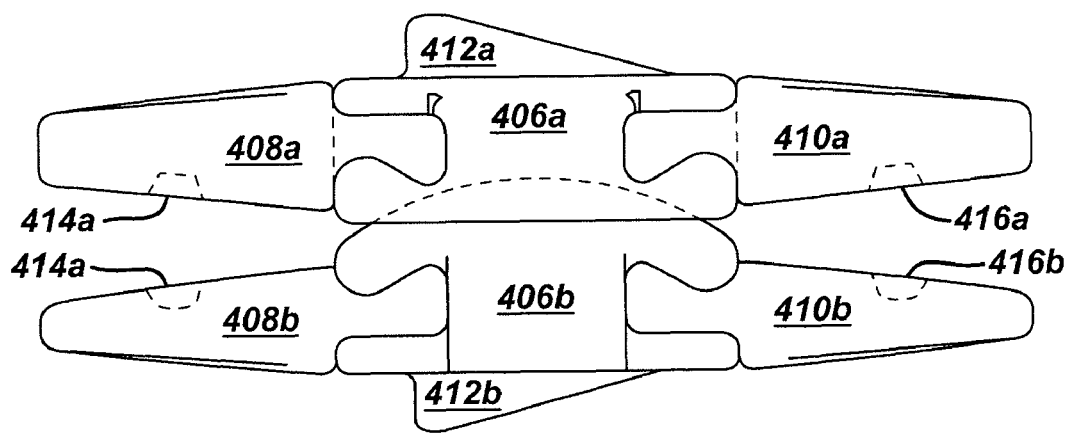
FIG. 4B is a side view of the implant shown in FIG. 4A.

FIGS. 4A-4B illustrate another embodiment of an implant having a central component and first and second lateral components. In this embodiment, the implant 400 includes left and right lateral components that mate to the central component. In particular, the central component includes superior and inferior members 406a, 406b, the left lateral component includes superior and inferior lateral members 408a, 408b, and the right lateral component includes superior and inferior lateral members 410a, 410b.

Figure 4E:
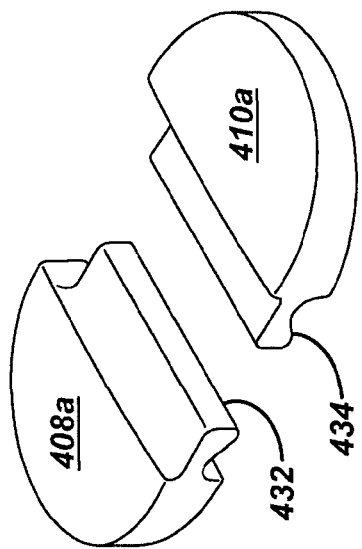
FIG. 4E is a perspective view of first and second superior lateral components of the implant shown in FIGS. 4A-4B.
Figure 4F:
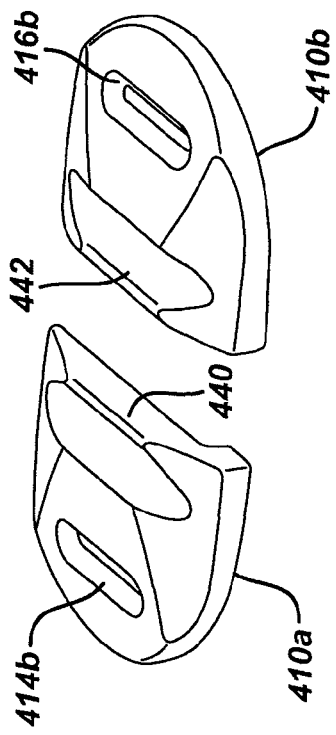
FIG. 4F is a perspective view of first and second inferior lateral components of the implant shown in FIGS. 4A-4B.
Figure 4C:
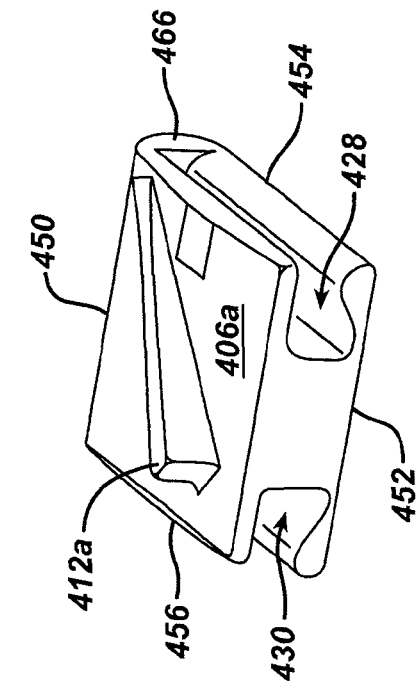
FIG. 4C is a perspective view of a superior central component of the implant shown in FIGS. 4A-4B.
Figure 4D:
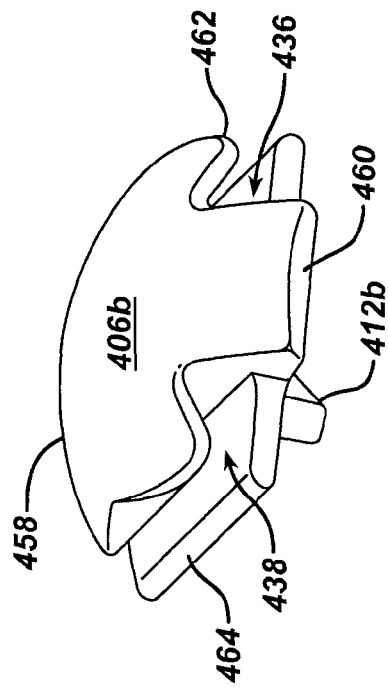
FIG. 4D is a perspective view of an inferior central component of the implant shown in FIGS. 4A-4B.

The superior and inferior central members 406a, 406b, which are shown in more detail in FIGS. 4C and 4D, respectively, are similar to the superior and inferior central members 12, 14 previously described with respect to FIGS. 1A and 1B. The members 406a, 406b, however, each have a generally square or rectangular shape with opposed leading and trailing ends 450, 452, 458, 460 and opposed lateral sides 454, 456, 462, 464 extending therebetween. Each central member 406a, 406b can include an articular surface to allow the superior and inferior central members 406a, 406b to move relative to one another. FIG. 4C illustrates a concave recess formed in the superior central member 406a, and FIG. 4D illustrates a convex surface formed on the inferior central member 406b. The convex surface can be movably disposed within the concave recess to allow movement between the superior and inferior central members 406a, 406b, and thereby allow movement between adjacent superior and inferior vertebrae between which the implant 400 is disposed. As with the embodiment shown in FIGS. 1A-1B, the central members 406a, 406b can also have a size that allows the central members to be introduced through a posterolateral access window. The size can also be configured to allow the leading and trailing ends 450, 452, 458, 460 of the central members 406a, 406b to contact cortical bone surrounding the disc space in which the implant 400 is inserted. The central members 406a, 406b can also include other features to facilitate use of the implant 400, such as one or more keels 412a, 412b formed on the bone-contacting surfaces of the central members 406a, 406b to facilitate insertion of the implant 400, similar to those described above in relation to FIGS. 1A-1C.

The superior left and right lateral members 408a, 408b are shown in more detail in FIG. 4E, and the inferior left and right lateral members 410a, 410b are shown in more detail in FIG. 4F. As shown, each lateral member 408a, 408b, 410a, 410b has a semi-circular shape with a substantially straight edge and a curved portion extending between the ends of the straight edge. Such a shape allows the lateral members to mate to the central component to thereby form a disc implant that substantially occupies a disc space, i.e., that has a footprint that matches a footprint of an endplate of a vertebra, as will be discussed in more detail below. As further shown, the straight edge of each lateral member 408a, 408b, 410a, 410b includes a mating element that is adapted to allow each lateral member 408a, 408b, 410a, 410b to mate to the corresponding mating elements formed on or within the opposed lateral sides of the central members 406a, 406b. While various mating techniques can be used, FIGS. 4A-4F illustrate a tongue-and-groove connection similar to that previously described with respect to FIGS. 3A-3B. In particular, the superior central member 406a includes grooves 428, 430 formed within opposed lateral sides 454, 456 thereof, and the inferior central member 406b includes grooves 436, 438 formed within opposed lateral sides 462, 464 thereof. Each groove 428, 430, 436, 438 is sized to receive a complementary tongue 432, 434, 440, 442 formed on a lateral member 408a, 408b, 410a, 410b. Each tongue 432, 434, 440, 442 extends along the length of the lateral members 408a, 408b, 410a, 410b. The mating elements can also include a stop that is adapted to prevent the lateral members 408a, 408b, 410a, 410b from sliding past the leading end of the central members 406a, 406b. FIG. 4C illustrates a stop 466 that forms a terminal end surface of the groove 428 in the superior central member 406a.

Figure 4G:
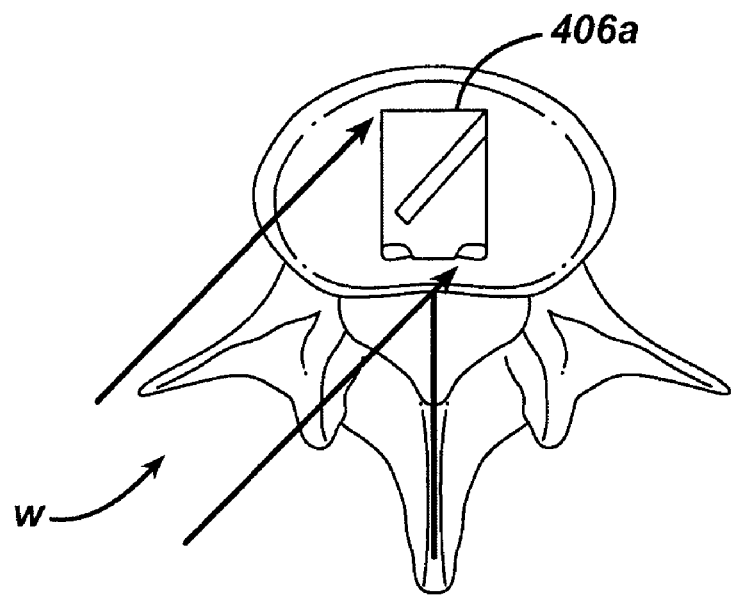
FIG. 4G is a top view of the superior and inferior central components of FIGS. 4C and 4D positioned on a vertebral body, showing a posterolateral surgical access window for introducing the central components.
Figure 4H:
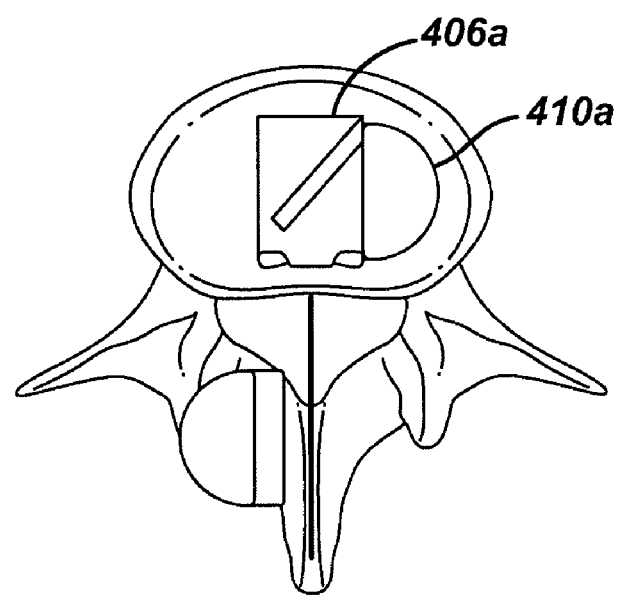
FIG. 4H is top view of the central components and vertebral body of FIG. 4G showing one of the superior and one of the inferior lateral components of FIGS. 4E and 4F mated to a first side of the central component.

FIGS. 4G-4H illustrate the implant in use. As shown in FIG. 4G, the central members (only superior member 406 is shown) of the implant 400 are introduced along an axis of a posterolateral surgical access window w to position the central component between the adjacent vertebra. As shown in FIG. 4F, the right superior and inferior lateral members (only superior member 410a is shown) is introduced using a posterior approach to mate the lateral members to the central members. The left superior and inferior lateral members 408a, 408b (not shown) can then be introduced on the contralateral side of the vertebra using a posterior approach to mate the left lateral members to the opposed side of the central members 406a, 406b. When mated, the central members 406a, 406b and the lateral members 408a, 408b, 410a, 410b form an implant having a footprint that is substantially equal to a footprint of a vertebral endplate, i.e., the implant is substantially disc-shaped to increase contact with the endplates of the adjacent vertebrae.

Figure 5A:
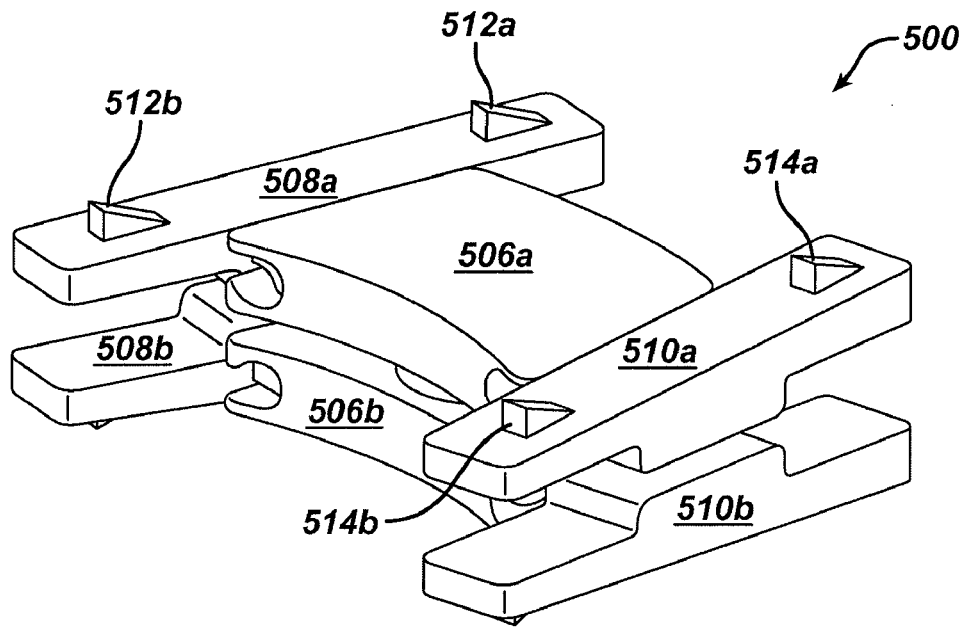
FIG. 5A is a perspective view of one exemplary embodiment of an implant that is configured to be inserted between adjacent vertebrae along a curved path using a posterolateral approach.
Figure 5B:
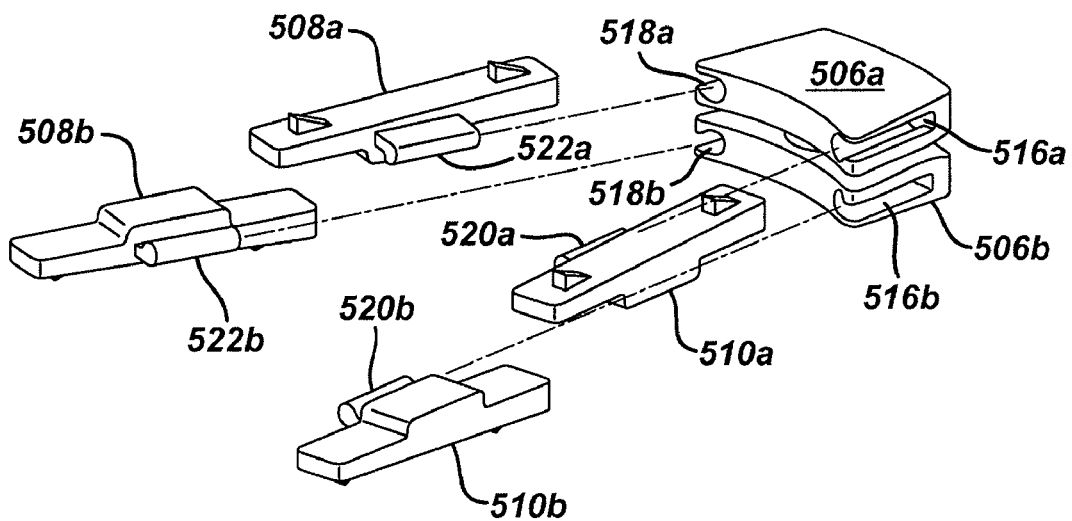
FIG. 5B is an exploded perspective view of the implant shown in FIG. 5A.

FIGS. 5A-5B illustrate another embodiment of an implant having a central component and left and right lateral components. In this embodiment, the central component of the implant 500 is substantially banana shaped and configured to be rotated once it is introduced into the disc space using a posterolateral approach. In particular, the central component includes superior and inferior central members 506a, 506b, which are shown in more detail in FIGS. 5C and 5D, respectively, that have a banana shape with curved posterior and anterior edges 518, 520, 522, 514, and lateral edges 530, 532, 534, 536 extending between the posterior and anterior edges 518, 520, 522, 514. The maximum width $w_5$ extending between the posterior and anterior edges 518, 520, 522, 514 of each member 506a, 506b is sized to allow the implant 500 to be introduced through a posterolateral access window without distracting nerves and dural elements with lateral edges 530, 536 leading, or with lateral edges 532, 534 leading. By way of non-limiting example, the maximum width $W_5$ can be about 13 mm. As the central members 506a, 506b approach or are within the disc space, the central members 506a, 506b can be turned to position the anterior edges 520, 514 adjacent to the anterior side of the disc space, and to position the posterior edges 518, 522 adjacent to the posterior side of the disc space. The curved configured can facilitate rotation of the central members 506a, 506b, however a person skilled in the art will appreciate that the central members 506a, 506b can have straight edges, or any other configuration that allows it to be introduced in a first orientation, and to be rotated into a second orientation within the disc space.

Figure 5E:
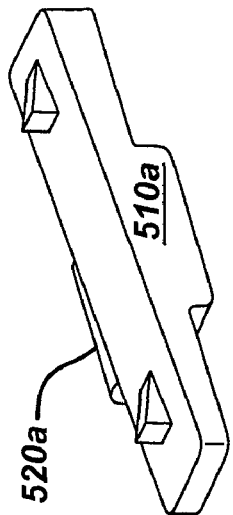
FIG. 5E is a perspective view of a superior lateral component of the implant shown in FIGS. 5A-5B.
Figure 5F:
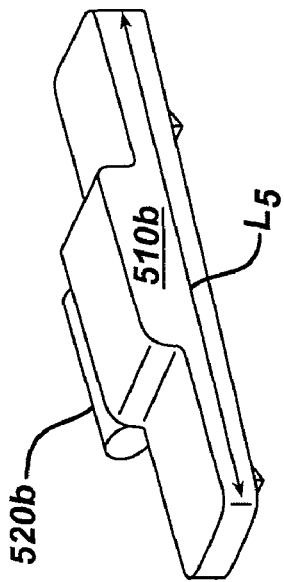
FIG. 5F is a perspective view of an inferior lateral component of the implant shown in FIGS. 5A-5B.
Figure 5C:
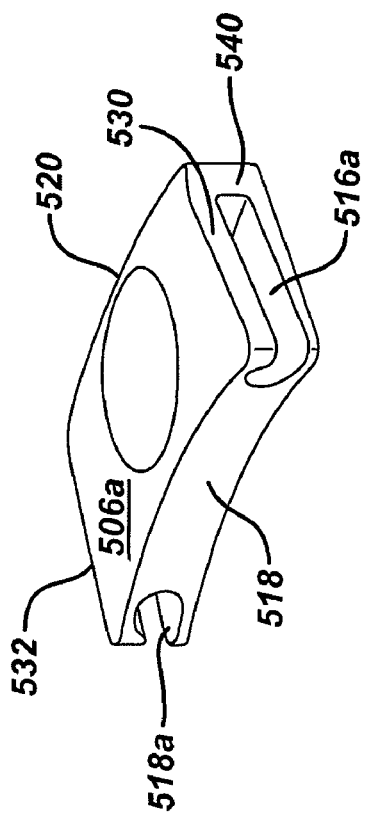
FIG. 5C is a perspective view of a superior central component of the implant shown in FIGS. 5A-5B.
Figure 5D:
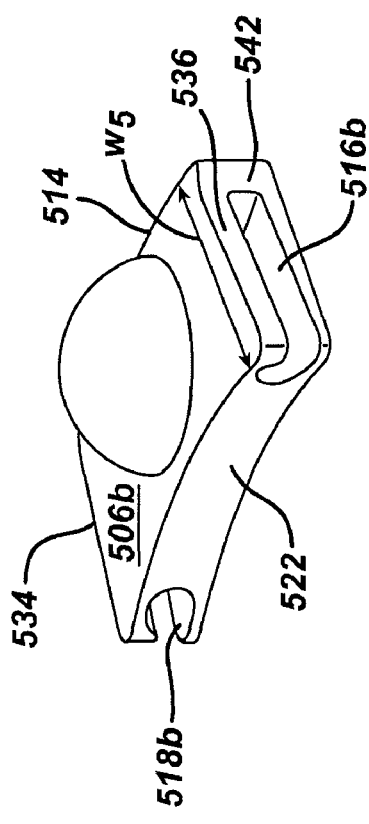
FIG. 5D is a perspective view of an inferior central component of the implant shown in FIGS. 5A-5B.

Once the central members 506a, 506b are implanted in the disc space and positioned properly, the left and right lateral components can be attached to the lateral edges 530, 532, 534, 536 of the central members 506a, 506b. A superior lateral member 510a is shown in FIG. 5E, and an inferior lateral member 510b is shown in FIG. 5F. As shown, each lateral member 510a, 510b has a generally elongate, rectangular configuration with a length $L_5$ that is greater than a width $w_5$ of the central members 506a, 506b. This allows the lateral members 508a, 508b, 510a, 510b to provide additional contact between the implant and the endplates of the adjacent vertebrae. The lateral members 508a, 508b, 510a, 510b can also help stabilize the central members 506a. 506b. In order to mate the lateral members 508a, 508b, 510a, 510b to the central members 506a, 506b, FIGS. 5A-5F illustrate grooves 516a, 516b, 518a, 518b formed on or within the central members 506a, 506b and complementary tongues 520a, 520b, 522a, 522b disposed on the lateral members 508a, 508b, 510a, 510b, similar to those described above in relation to FIGS. 4A-4F, for mating the components. FIGS. 5C and 5D also illustrated a stop surface 540, 542 formed at a terminal end of each groove 516a, 516b for preventing the lateral members 508a, 508b, 510a, 510b for sliding past the central members 506a, 506b. The stop surface can be formed by merely terminating the grooves 516a, 516b prior to the anterior edge 520, 514 of the central members 506a, 506b. A person skilled in the art will appreciate that other mating techniques can be used.

The implant can also include other features, such as keels 512a, 512b, 514a, 514b formed on the lateral members 508a, 508b, 510a, 510b. The keels can facilitate insertion of the lateral members, and they can also optionally function as bone-engaging surface features to mate the lateral members to the endplates of the adjacent vertebrae. While not shown, the central members 506a, 506b can also include keels or other features to facilitate insertion and implantation thereof.

Figure 6:
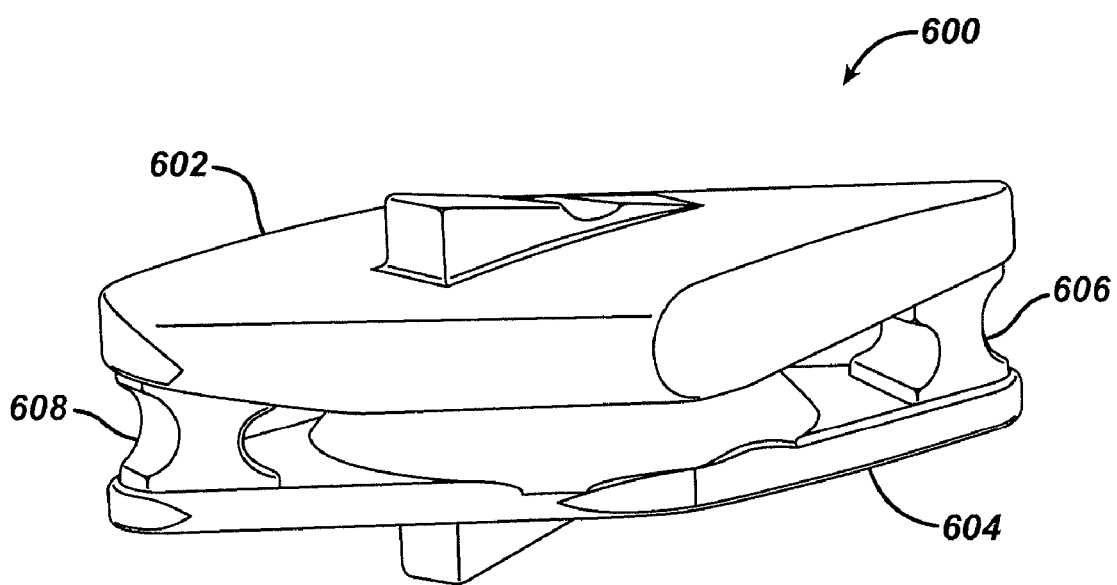
FIG. 6 is a perspective view of yet another exemplary embodiment of an implant that can be introduced between adjacent vertebrae using a posterolateral approach, showing struts extending between superior and inferior members of the implant to provide rotational control during movement of adjacent vertebrae.

In other embodiments, the various implants disclosed herein can include features to provide rotational control during movement of the adjacent vertebrae. For example, an elastomer structure, compressible element, spring, or other member can extend between and couple to the various superior and inferior members of the implant. By way of non-limiting example, FIG. 6 illustrates one embodiment of an implant 600 that is similar to the implant of FIGS. 1A-1B, but that includes first and second elastomer struts 606, 608 that extend between the articular surfaces of the superior and inferior members 602, 604. The struts 606, 608 can be positioned at any location, but they are preferably positioned on opposite sides of the implant 600 to provide uniform rotational control of the adjacent vertebrae. As shown in FIG. 6, the first strut 606 is positioned adjacent to the leading end of the implant, and the second strut 608 is positioned adjacent to the trailing end of the implant. The struts 606, 608 can be formed integrally with the superior and inferior members 602, 604, or they can be bonded to the superior and inferior members 602, 604 using various mating techniques known in the art. In other embodiments, the strut(s) can be removably mated to the implant to allow insertion of the members individually. Where the implant includes one or more lateral components, the struts can be formed or disposed between the superior and inferior lateral members. The embodiment previously shown in FIGS. 3A-3C illustrates a strut 312 which extends between the superior and inferior lateral members 308a, 308b. The strut 312 is positioned at a location opposite to the mating elements on the lateral members 308a, 308b.

Figure 7A:
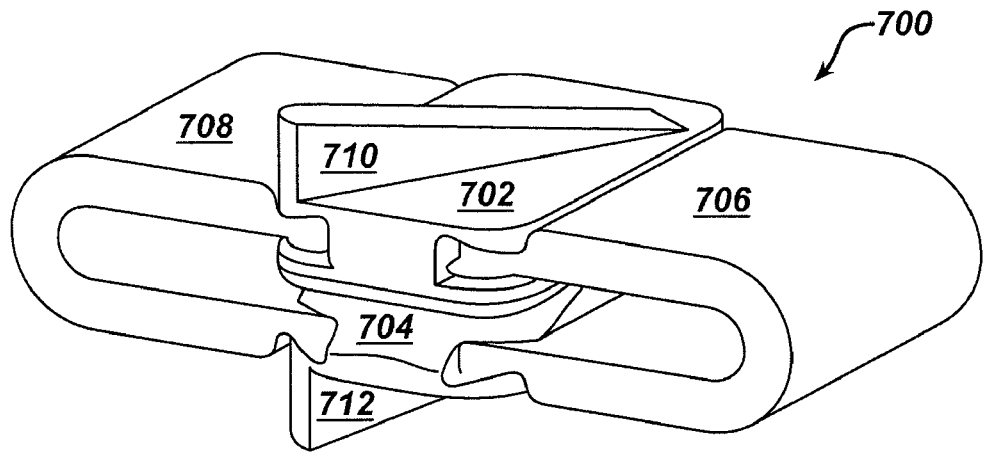
FIG. 7A is a perspective view of one exemplary embodiment of an implant having a central component that can introduced between adjacent vertebrae using a posterolateral approach and having lateral components in the form of springs that mate to the central component.
Figure 7B:
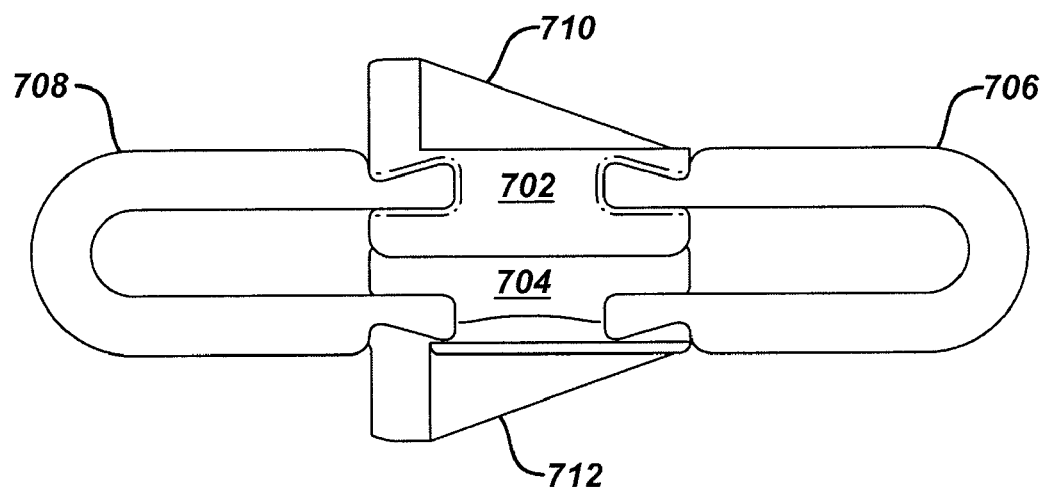
FIG. 7B is a side view of the implant shown in FIG. 7A.

FIGS. 7A and 7B illustrate another embodiment of a technique for providing rotational control. In this embodiment, the implant 700 includes superior and inferior central members 702, 704 similar to those described above in relation to FIGS. 4A-4F, and first and second lateral components 706, 708 that are in the form of springs. In particular, each lateral components 706, 708 is substantially U-shaped and includes terminal ends that slidably mate to the superior and inferior central members 702, 704. While various mating techniques can be used, FIGS. 7A-7B, illustrates a tongue-and-groove mating connection. In use, the lateral components 706, 708 can provide rotational control as the central members 702, 704 articulate relative to one another in coordination with movement of the adjacent vertebrae.

A person skilled in the art will appreciate that the implants disclosed herein can have a variety of other configurations. For example, a separate insert, such as a floating core, can be inserted between the central members to allow movement therebetween. Alternatively, the implant or central component of the implant can be formed from a single, unitary member that either allows, limits, or prevents movement between adjacent vertebrae. The lateral component(s) can likewise be formed from a single unitary member that merely mates to the central component to maximize contact with the endplates of the adjacent vertebrae.

Various exemplary instruments for introducing an implant using a posterolateral approach are also provided, as well as various exemplary methods for using such instruments. In general, the instruments are configured to interconnect to an implant and/or to a guide member such that the components are all docked relative to one another. This allows the various components of a multi-piece implant to be mated intraoperatively within the disc space, and in particular to be guided into alignment with one another.

FIGS. 8-13 illustrates various exemplary tools for introducing and intraoperatively mating various components of an implant to one another. The illustrated tools are particularly configured for use with the implant 500 of FIGS. 5A and 5B, however a person skilled in the art will appreciate that the tools can be used with a variety of implants, and each tool can be customized based on the particular configuration of the implant.

Figure 8A:
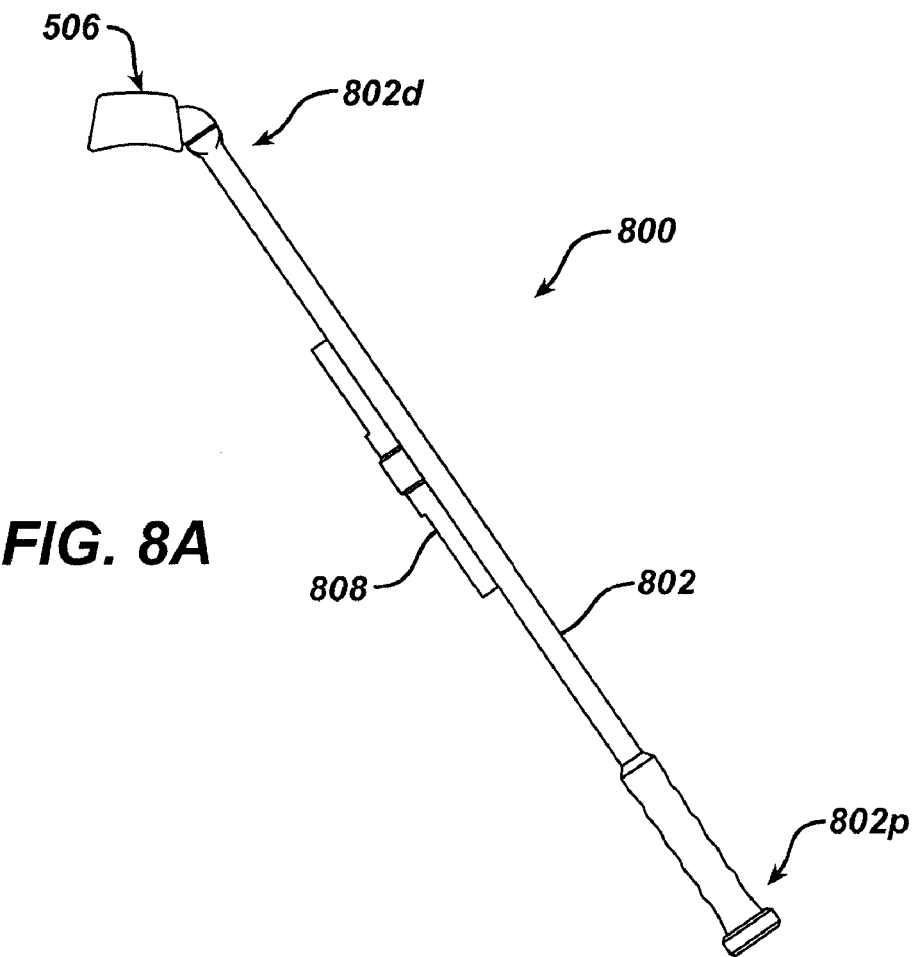
FIG. 8A is a perspective view of one embodiment of a central inserter tool shown mated to a central component of the implant of FIGS. 5A and 5B.
Figure 8B:
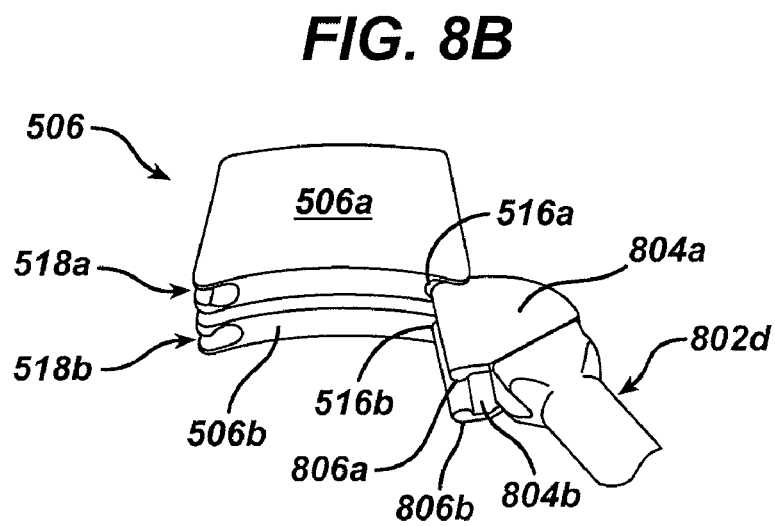
FIG. 8B is an enlarged view of a distal end of the central inserter tool and the central component of FIG. 8A.

FIGS. 8A and 8B illustrate one embodiment of a central inserter tool 800 that is adapted to mate to the central members 506a, 506b (collectively referred to as central component 506) of the implant 500 of FIGS. 5A and 5B, as shown, and that is adapted to introduce the central component 506 into a disc space between adjacent vertebrae. As shown, the central inserter tool 800 has a generally elongate shaft 802 with proximal and distal ends 802p, 802d. The length of the shaft 802 can vary, but in an exemplary embodiment the proximal end 802p is adapted to remain outside of the patient's body while the distal end 802d is inserted into a disc space. The proximal end 802p can include a handle formed thereon to facilitate grasping and manipulation of the device, and the distal end 802d can include features to engage and mate to the central component 506. In an exemplary embodiment, as shown in more detail in FIG. 8B, the distal end 802d includes first and second tabs 804a, 804b formed thereon and having tongues 806a, 806b adapted to slidably fit within two of the grooves 516a, 516b, 518a, 518b (i.e., within groves 518a, 518b as shown) formed on or within the central members 506a, 506b of the central component 506. The tabs 804a, 804b are preferably spaced a distance apart from one another such that the tabs 804a, 804b are effective to maintain the superior and inferior central members 506a, 506b in alignment with and at a predetermine position relative to one another. The predetermined position is preferably the position at which the central members 506a, 506b are in contact with one another and are configured to be inserted into the disc space. The central inserter tool 800 can also include a guidewire channel formed thereon or therein for receiving a guidewire. FIG. 8A illustrates a guide tube 808 coupled to the shaft 802 of the central inserter tool 800 and having a guide channel or lumen formed therethrough for receiving a guidewire. A person skilled in the art will appreciate that a variety of other techniques can be used to mate a guidewire to the central inserter tool 800, and that the shaft 802, or portions thereof, can include one or more openings formed therein or various other features formed thereon.

Figure 9A:
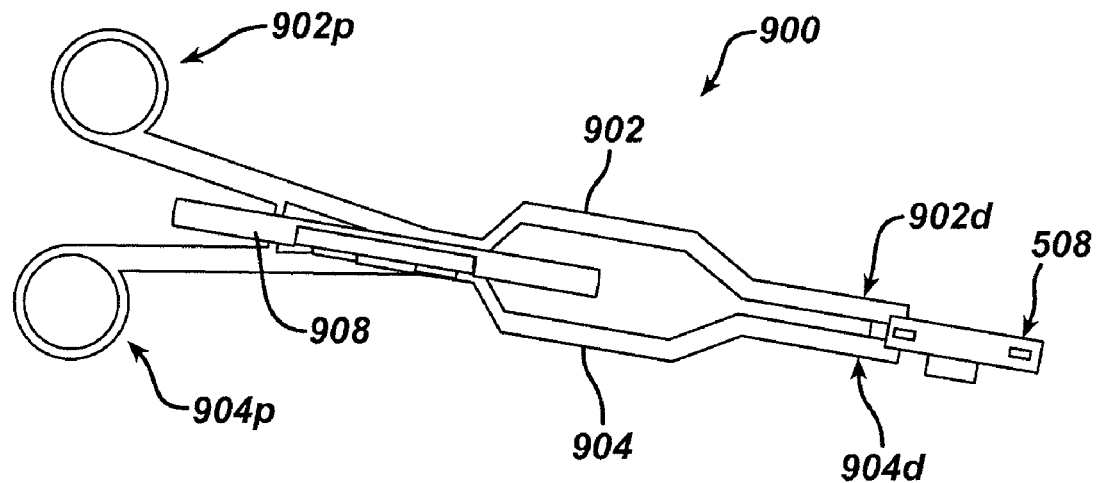
FIG. 9A is a perspective view of one embodiment of a lateral inserter tool shown mated to a lateral component of the implant of FIGS. 5A and 5B.
Figure 9B:
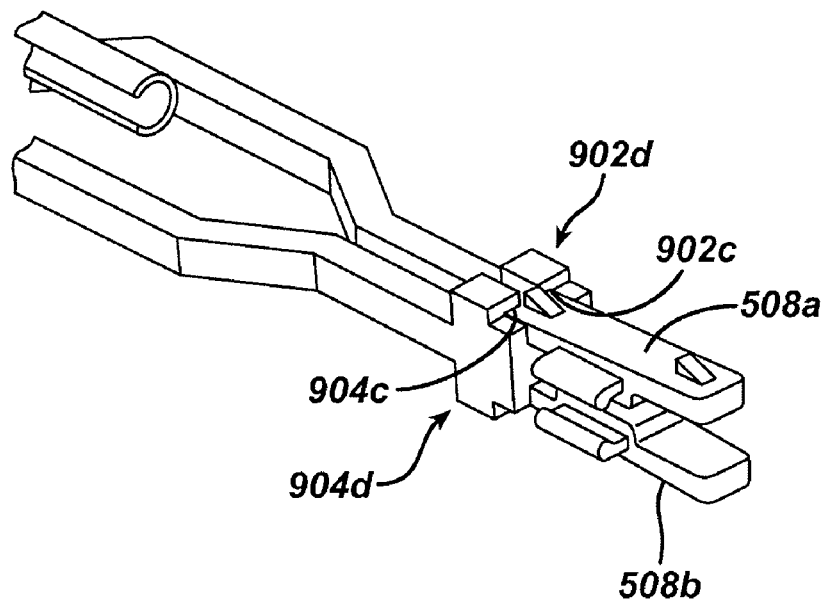
FIG. 9B is an enlarged view of a distal end of the lateral inserter tool and the lateral component of FIG. 9A.

FIGS. 9A and 9B illustrate one embodiment of a lateral inserter tool 900 that is adapted to mate to a lateral component, i.e., the left superior and inferior lateral members 508a, 508b (collectively referred to as the lateral component 508) as shown, or the right superior and inferior lateral members 510a, 510b (collectively referred to as the lateral component 510) of FIGS. 5A and 5B. In use, the lateral inserter tool 900 is adapted to introduce one of the lateral components 508, 510 into a disc space between adjacent vertebrae to mate the lateral component to the central component. The lateral inserter tool 900 can have a variety of configurations, but in the illustrated embodiment the lateral inserter tool 900 includes first and second arms 902, 904 that are pivotally coupled to one another at a mid-portion thereof. Like the central inserter, the length of the arms 902, 904 can vary, but in an exemplary embodiment the proximal ends 902p, 904p are adapted to remain outside of the patient's body while the distal ends 902d, 904d are inserted into a disc space. Each arm 902, 904 can include a proximal end 902p, 904p that can have a handle, such as a finger loop or various other grasping elements, formed thereon, and a distal end 902d, 904d that is adapted to engage a lateral component. While various techniques can be used to engage the lateral members 508a, 508b (or 510a, 510b) between the distal ends 902d, 904d, in the illustrated embodiment, as shown in more detail in FIG. 9B, each distal end 902d, 904d includes a cavity 902c, 904c formed therein. The cavities 902c, 904c can be opposed to and can face one another such that, when the distal ends 902d, 904d are moved together, an end portion of the lateral component 508 can be engaged between the cavities. Movement of the distal ends 902d, 904d toward one another can be achieved by moving the proximal end 902p, 904p of each arm 902, 904 toward one another. Conversely, movement of the arms 902p, 904p away from one another will move the distal ends 902d, 904d apart, thereby allowing the lateral component 508 to be received therebetween or to be released. The cavities 902c, 904c can also have a shape that is effective to hold the lateral members 508a, 508b of the lateral component 508 at a predetermined position relative to one another such that, when inserted into a disc space, the lateral members 508s, 508b are properly positioned so as to be aligned with the central members 506a, 506b of the central component 506 to allow easy mating between the components. The lateral inserter tool 900 can also include a guidewire channel formed thereon or therein for receiving a guidewire. FIG. 9A illustrates a guide tube 908 coupled between the first and second arms 902, 904 of the lateral inserter tool 900 and having a guide channel or lumen formed therethrough for receiving a guidewire. The guide tube 908 is preferably positioned in alignment with the cavities 902c, 904c such that a guidewire can extend through the guide tube 908 and through the lateral component. A person skilled in the art will appreciate that a variety of other techniques can be used to mate a guidewire to the central inserter tool 800, and that the shaft 802, or portions thereof, can include one or more openings formed therein or various other features formed thereon. Again, a person skilled in the art will appreciate that a particular configuration of the lateral inserter tool can vary depending on the particular configuration of the implant.

Figure 10:
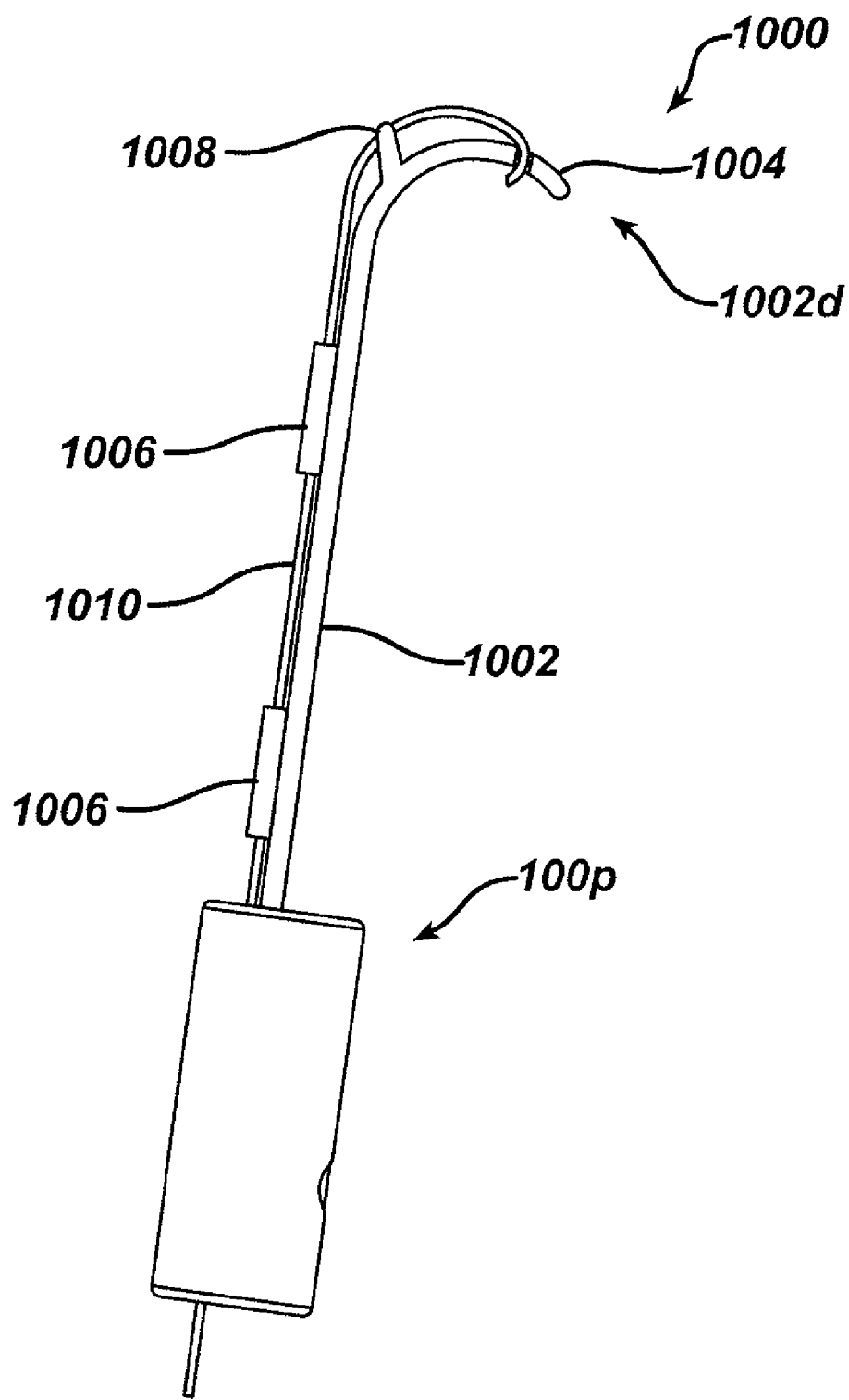
FIG. 10 is a perspective view of one embodiment of a guidewire inserter tool having a guidewire coupled thereto.
Figure 11:
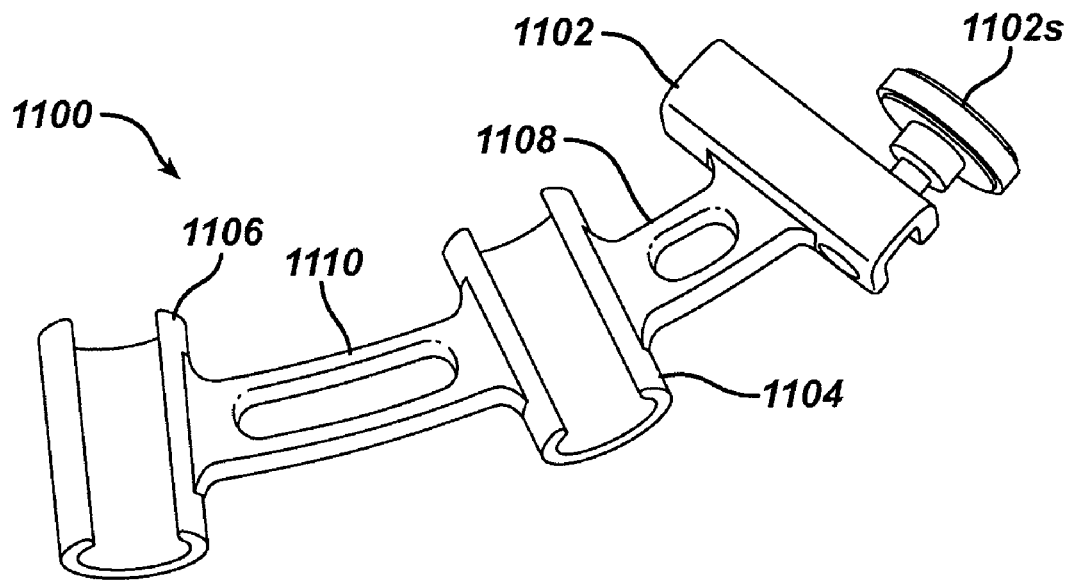
FIG. 11 is a perspective view of one embodiment of a guide frame for mating to a central inserter tool and for guiding one or more lateral inserters tools into a disc space.

FIGS. 10 and 11 illustrate exemplary embodiments of guide devices that can be used to interconnect the implant, or portions thereof, with the central inserter tool and the lateral inserter tool to facilitate alignment of the tools and thus mating of the implant components intraoperatively within a disc space. In particular, the guide devices can connect to one of the other components of the system, such as the implant and/or one of the inserter tools so that all of the components are interconnected to one another, either directly or indirectly through another component. Such a "docking" configuration allows the components to be properly aligned during insertion without the need for visual access to the implant site, as will be discussed in more detail below.

In the embodiment shown in FIG. 10, the guide device is in the form of a guidewire inserter tool 1000 for positioning a guide wire within a disc space, and for guiding the central inserter tool and central component into the disc space. As shown, the guidewire inserter tool 1000 includes a generally elongate shaft 1002 having a proximal end 1002p with a handle formed thereon to facilitate grasping of the device, and a distal end 1002d with a curved or C-shaped terminal portion 1004 formed thereon. The curved portion 1004 is preferably shaped so as to avoid contact with the spinal cord during insertion into a disc space, and to facilitate positioning of the central component within the disc space. In particular, the curved portion 1004 can complement the curved posterior edge 518, 522 of the central members 506a, 506b to allow the central members 506a, 506b of the central component to be positioned there against when inserted into the disc space. This can facilitate proper alignment both medial-laterally and in the posterior-anterior direction. As further shown, the guidewire inserter tool 1000 can also includes a guide channel for slidably receiving a guidewire 1010. In the illustrated embodiment, the handle on the proximal end 1002p includes a bore (not shown) formed therethrough, and the shaft 1002 includes several tubular members 1006 disposed thereon along the length thereof. The guidewire 1010 is passed through the handle and the through tubular members 1006 so that it extends along the entire length of the shaft 1002 to allow a distal or terminal end of the guidewire 1010 to be positioned within the disc space, as will be discussed in more detail below. The guidewire 1010 can also extend through a stop 1008 formed on the curved portion 1004. The stop 1008 can be effective to limit insertion of the central component 506 into the disc space, as will be discussed in more detail below. In use, the guidewire can be positioned within the disc space, and it can interconnect the central inserter tool and central component with one or more lateral inserter tools. In particular, and as will be discussed in more detail below, the guidewire can mate to the central inserter tool 800 and central component, and the lateral inserter tool 900 can be advanced along the guidewire to mate the lateral component to the central component. Upon removal of the central inserter tool 800 from the guidewire, the guidewire can also guide a second lateral inserter tool into the disc space to mate a second lateral component to the central component. A person skilled in the art will appreciate that the particular configuration of the guidewire inserter tool can vary, and that the tool can simply be configured to introduce a guidewire into a disc space, or it can include features to further facilitate positioning of an implant, or portion thereof, within a disc space.

FIG. 11 illustrates another embodiment of a guide device. In this embodiment, the guide device is in the form of a frame 1100 that is adapted to mate to the central inserter tool, and that includes one or more guide channels for guiding one or more lateral inserter tools into the disc space to align the lateral component(s) 508, 510 with the central component 506. In general, the frame 1100 has an elongate configuration with three channels 1102, 1104, 1106 that are connected to one another by cross-bars 1108, 1110. The first channel 1102 can be configured to removably mate to the central inserter tool 800 of FIG. 8A. In the illustrated embodiment, the first channel 1102 has a generally elongate rectangular shape with one of the sidewalls removed so as to allow positioning of the central inserter tool 800 therein. The first channel 1102 can also include a locking mechanism, such as a locking screw 1102s, formed thereon or coupled thereto for selectively locking the central inserter tool 800 thereto. This will allow the frame 1100 to be fixedly attached to the central inserter tool 800. The second channel 1104 can be spaced a distance apart from the first channel 1102 and maintained at that position by cross-bars 1108. In an exemplary embodiment, the second channel 1104 is positioned at an angle relative to the first channel, and the particular angle is configured so as to align a lateral component 508, 510 mated to a lateral inserter tool inserted through the second channel 1104 with the central component 506 so that the lateral component can be easily slid into and mated to a lateral side of the central component. The third channel 1106 can likewise be spaced a distance from the second channel 1104 and it can be maintained in that position by cross-bars 1110. The third channel 1106 can also be positioned at an angle relative to the first and second channels 1102, 1104, and the particular angle can be selected so as to align a lateral component 508, 510 mated to a second lateral inserter tool inserted through the third channel 1106 with the central component 506 so that the second lateral component can be easily slid into and mated to a contralateral side of the central component 506. In other words, the second and third channels 1104, 1106 can have an angle relative to one another that corresponds to the angle between the opposed lateral sides of the central component 506. In use, as will be discussed in more detail below, the frame 1100 therefore interconnects the components and provides a docking system to align the lateral components 508, 510 of the implant 500 with the central component 506.

Figure 12:
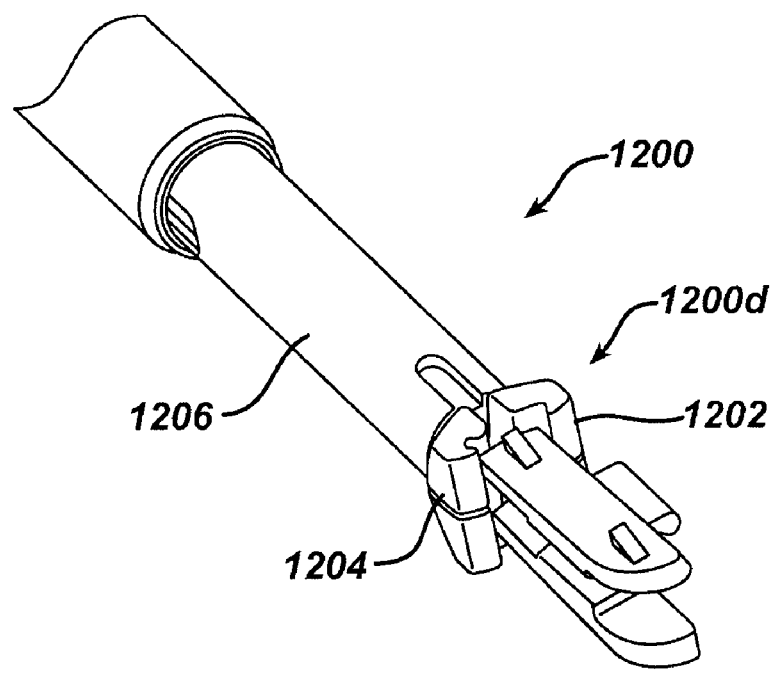
FIG. 12 is a perspective view of a distal portion of another embodiment of a lateral inserter tool for use with the guide frame of FIG. 11, shown mated to a lateral component of the implant of FIGS. 5A and 5B.

FIG. 12 illustrates another embodiment of a lateral inserter tool 1200 that is particularly configured for use with the guide frame 1100 of FIG. 11. While only a distal portion of the lateral inserter tool 1200 is shown, in this embodiment the inserter tool 1200 has a generally elongate shaft, rather that first and second arms. This allows the elongate shaft to be passed through one of the channels 1104, 1106 in the frame 1100. As with the previous lateral inserter tool 900, the distal end 1200d can include opposed arms 1202, 1204 that move relative to one another to engage superior and inferior members of a lateral component 508, 510 therebetween. In this embodiment, the arms 1202, 1204 can be deflectable relative to one another and they can be biased to an open position. An outer sleeve 1206 can be slidably disposed over the elongate shaft of the tool 1200, and it can be adapted to hold the arms 1202, 1204 together to thereby engage the lateral component. Again, a person skilled in the art will appreciate that a variety of other techniques can be used to engage a lateral component of an implant, and the particular configuration can vary depending on the configuration of the implant.

Figure 13:
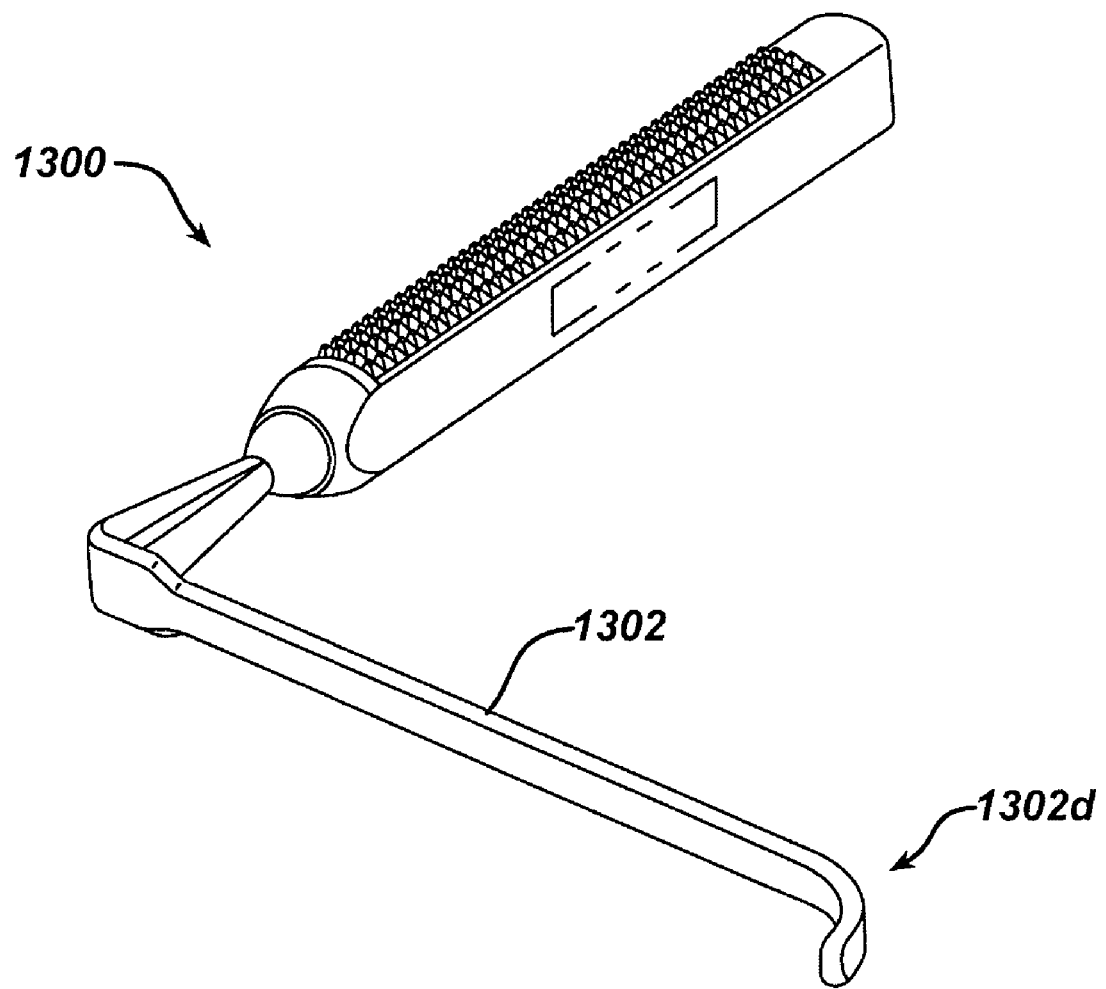
FIG. 13 is a perspective view of one embodiment of a retaining tool.

FIG. 13 illustrates another tool that can be used to facilitate intraoperative mating of a multi-piece implant within a disc space. In particular, FIG. 13 illustrates a retaining tool 1300 that is adapted to be positioned against an anterior surface of an implant (when using a posterior surgical approach) to retain or hold the implant in a fixed position. In the illustrated embodiment, the retaining tool 1300 has a generally elongate shaft 1302 with a curved distal end 1302d that is shaped to match or contour the shape of an anterior edge 520, 514 of the superior and inferior central members 506a, 506b of the central component 506 of the implant of FIGS. 5A and 5B. In an exemplary embodiment, the distal end 1302d has a height that is equal to a distance of the gap between the central members 506a, 506b, thereby allowing the distal end 1302d to be positioned within the gap to maintain the central members 506a, 506b at a predetermined position relative to one another (i.e., to prevent movement of the central members 506a, 506b relative to one another). The shaft 1302 can also include one or more bends or other curves formed therein as may be necessary to facilitate positioning of the shaft 1302 within the disc space.

Exemplary methods for replacing a spinal disc are also provided. In an exemplary embodiment, an incision is made at a posterolateral location in a patient back. A pathway is formed to the disc space by removing the facet joints, posterolateral annulus, and posterior lip, while leaving the remaining annulus and the anterior and posterior longitudinal ligaments in tact. The adjacent vertebrae are distracted, preferably on the contra-lateral side of the spine, and a discectomy is performed to remove the disc. The endplates can be prepared using various techniques known in the art. Where the implant includes a keel, grooves can be formed in the endplates to receive the keels therein. Once the disc space and endplates have been prepared, the implant or a component of the implant, e.g., the central component, can be introduced through the posterolateral access window. As previously explained, depending on the configuration of the implant, the implant can be introduced linearly along an axis of the access window, or it can curved once it is within the disc space to position it properly. Where the implant includes one or more lateral components, each lateral component can be introduced, preferably using a posterior approach. In one embodiment, the lateral components can be inserted along an axis that is substantially parallel to an axis of the spinous process. This is preferably done through a separate surgical access window formed on one or both sides of the spine.

FIGS. 14A-14I illustrate one exemplary method for intraoperatively mating a multi-piece implant within a disc space, and in particular FIGS. 14A-14I illustrate a method of implanting the implant 500 of FIGS. 5A and 5B using some of the various tools discussed above with respect to FIGS. 8-13, including a guidewire for interconnecting the various components during the procedure to allow for easy guidance of the implant components into mating alignment with one another. A person skilled in the art will appreciate that, while the method is described in connection with implant 500 and with the various tools previously discussed, the method can be used with any implant and using any tools.

Figure 14A:
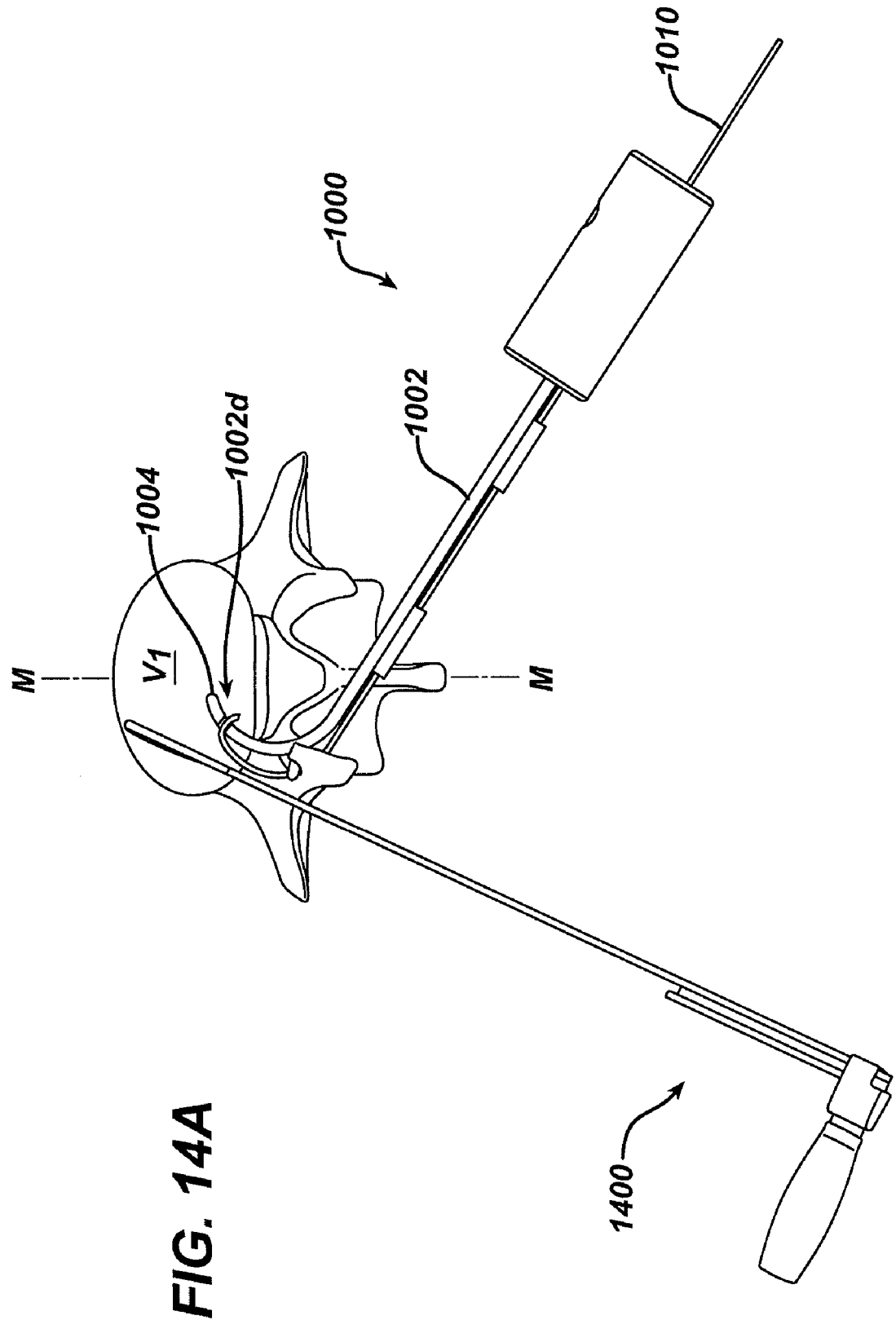
FIG. 14A is a top perspective view of a vertebra, showing a distractor positioned within the disc space, and showing the guidewire inserter tool of FIG. 10 being inserter into the disc space.
Figure 14B:
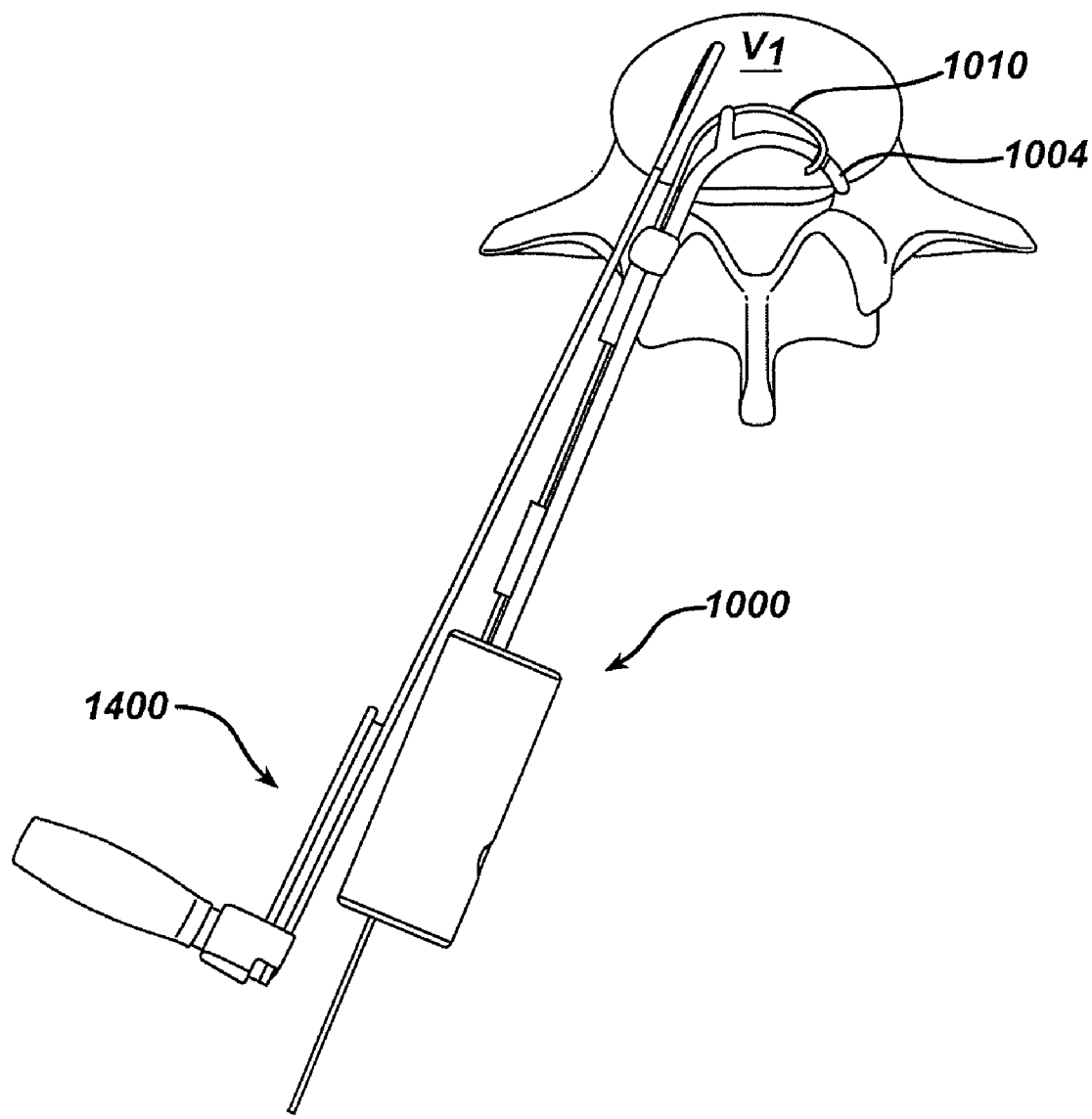
FIG. 14B is a top perspective view of the vertebra of FIG. 14A, showing the guidewire inserter tool positioned within the disc space.

As indicated above, at the outset the adjacent vertebrae are distracted and the disc space is prepared. Various distractor devices and techniques known in the art can be used to distract the adjacent vertebrae and to prepare the disc space. FIG. 14A illustrates a distractor 1400 disposed within the disc space to distract the adjacent vertebra (only one vertebra $V_1$ is shown). In an exemplary embodiment, the distractor 1400 is inserted along an axis that extends at an angle of about 30° to 35° from the midline M of the spine extending through the spinous process. Once the disc space is prepared, the guidewire inserter tool 1000, with the guidewire 1010 mated thereto, can be introduced into the disc space to position the curved portion 1004 on the posterior side of the disc space. In an exemplary embodiment, a set screw disposed through the handle of the guidewire inserter tool 1000 is used to lock the guidewire 1010 to the guidewire inserter tool 1000 prior to insertion into the disc space. The guidewire inserter tool 1000 can be inserted into the disc space on the same side as the distractor 1400 and it can be rotated during insertion to advance the curved portion 1004 around the spinal canal. FIG. 14B illustrates the guidewire inserter tool 1000 in its final position within the disc space, showing the curved portion 1004 positioned on a posterior side of the disc space. The position can optionally be confirmed using imagining techniques, such as fluoroscopy.

Figure 14C:
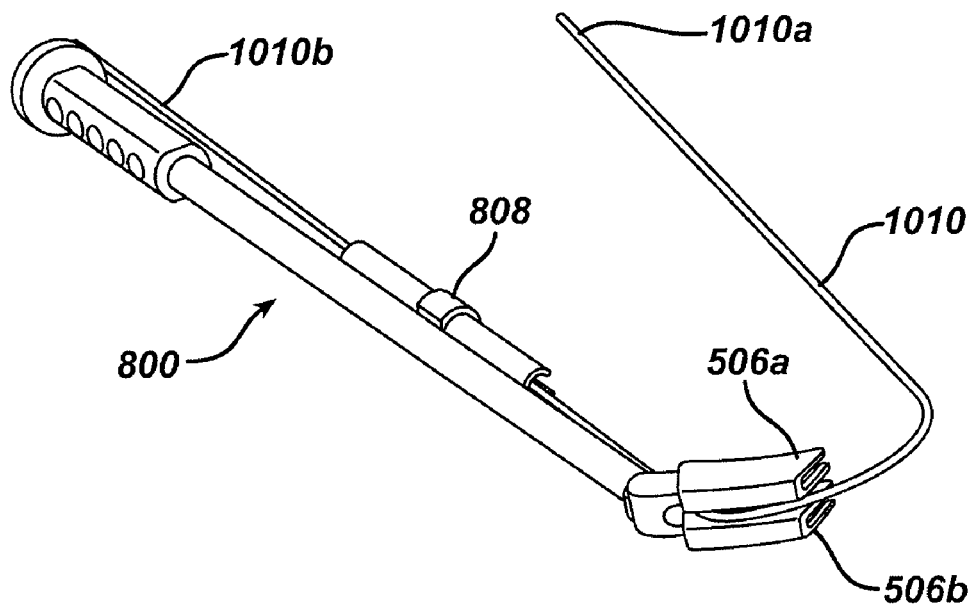
FIG. 14C is a perspective view of the central inserter tool and central component of FIG. 8A having the guidewire of the guidewire inserter tool of FIG. 10 coupled thereto.
Figure 14D:
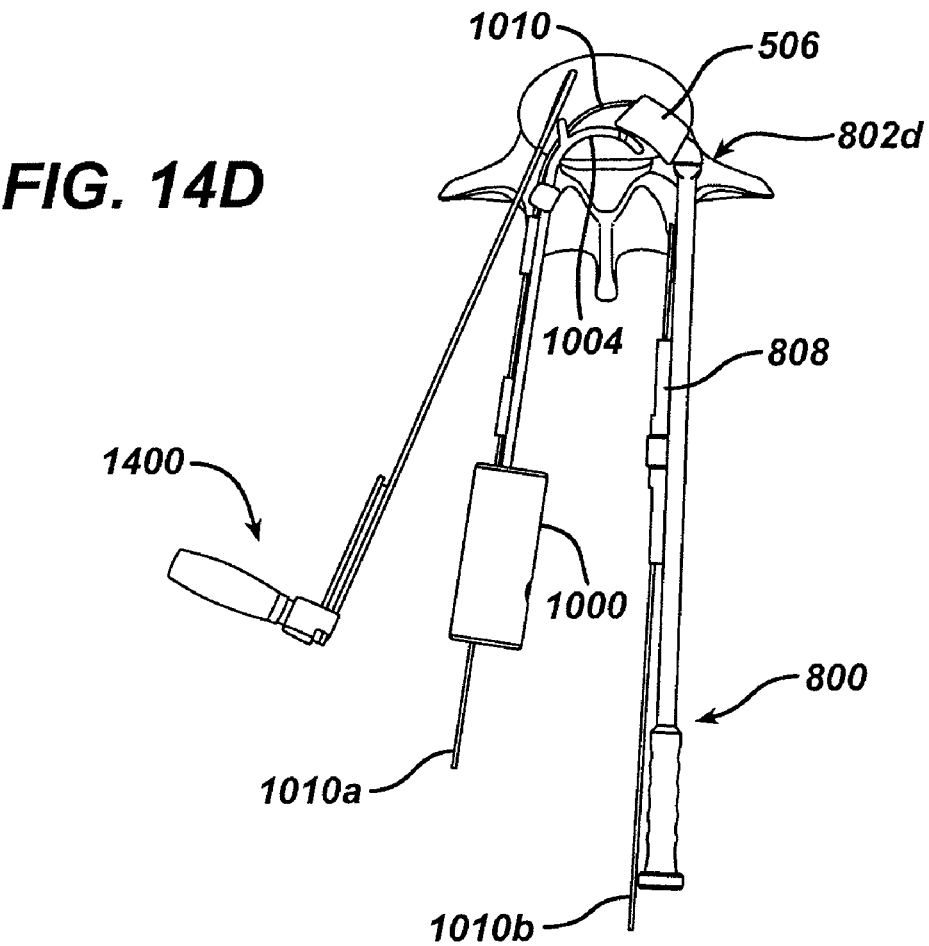
FIG. 14D is a top perspective view of the vertebra of FIG. 14B, showing the central inserter tool of FIG. 14C inserting the central component along the guidewire of the guidewire inserter tool and into the disc space.
Figure 14E:
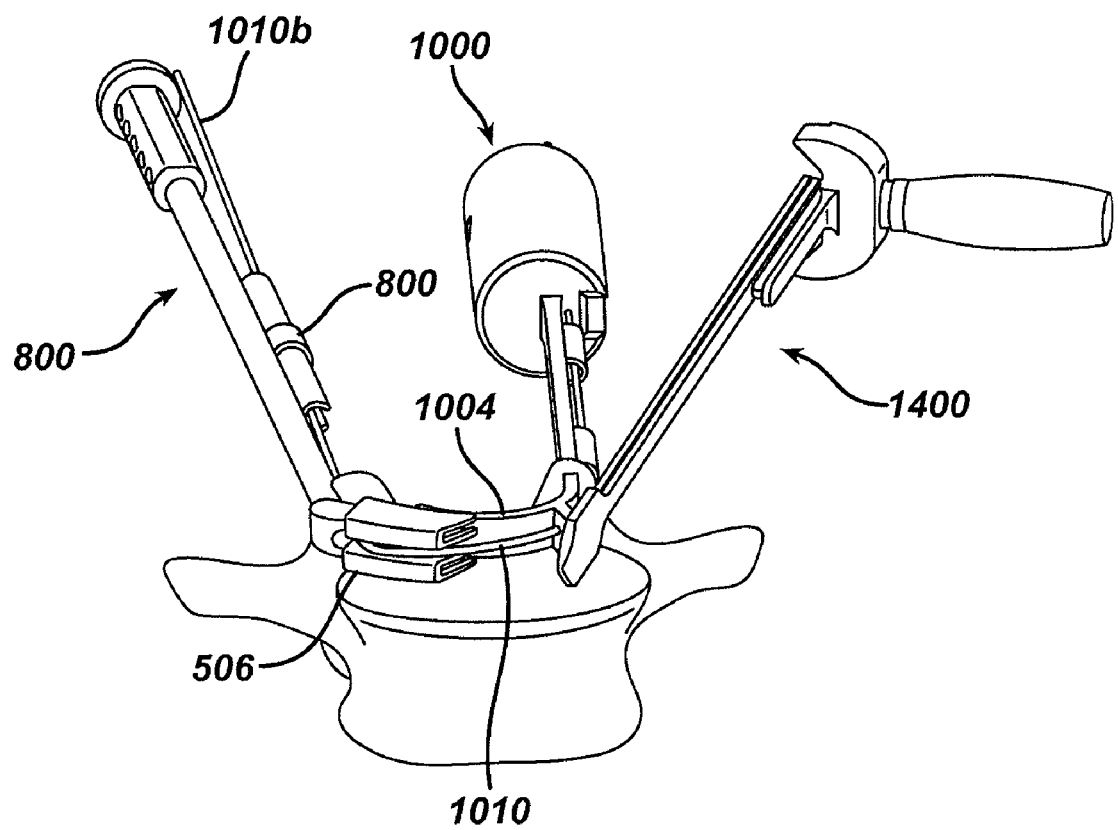
FIG. 14E is an anterior perspective view of the vertebra of FIG. 14D, showing the central inserter tool inserting the central component along the guidewire of the guidewire inserter tool and into the disc space.

Once the guidewire inserter tool 1000 is properly positioned, the guidewire 1010 can be unlocked, e.g., by releasing the set screw, to allow the guidewire 1010 to slide relative to the tool 1000. A grasping or similar device can be inserted into the disc space on a contralateral side of the vertebra, and it can be used to grasp and pull the free end of the guidewire 1010 out of the disc space so that the guidewire 1010 has two terminal ends 1010a, 1010b extending from opposed lateral sides of the disc space with a u-shaped central portion positioned within the disc space, as shown in FIG. 14D. The free terminal end of the guidewire 1010, i.e., the end 1010b not disposed through the guidewire inserter tool 1000, can then be positioned between and along the anterior side of the central members 506a, 506b of the central component 506, as shown in FIG. 14C and threaded through the guide tube 808 on the central inserter 800. While applying tension to the guidewire 1010, i.e., by pulling both ends 1010a, 1010b of the guidewire 1010 or by locking one end 1010a to the guidewire inserter tool 1000 and pulling the other end 1010b, the central inserter tool 800 can be advanced, i.e., slid, along the guidewire 1010 to insert the central component 506 into the disc space. The guidewire 1010 will guide the central component 506 into the disc space, positioning the central component 506 along an anterior side of the curved portion 1004 of the guidewire inserter tool 1000, as shown in FIG. 14D. As best shown in FIG. 14E, the central component 506 will extend between the guidewire 1010 and the curved portion 1004. Once fully inserted, the central component 506 will abut against the stop 1008 on the guidewire inserter tool 1000. The central inserter tool 800 can also be retracted once the distal end 802d is within the disc space to ensure that the central component 506 abuts against the curved portion 1004 of the guidewire inserter tool 1000, thereby ensuring proper positioning of the central component 506 in both a medial-lateral direction and a posterior-anterior direction. Again, fluoroscopy or other imagining techniques can optionally be used to confirm the position of the central component 506.

Figure 14F:
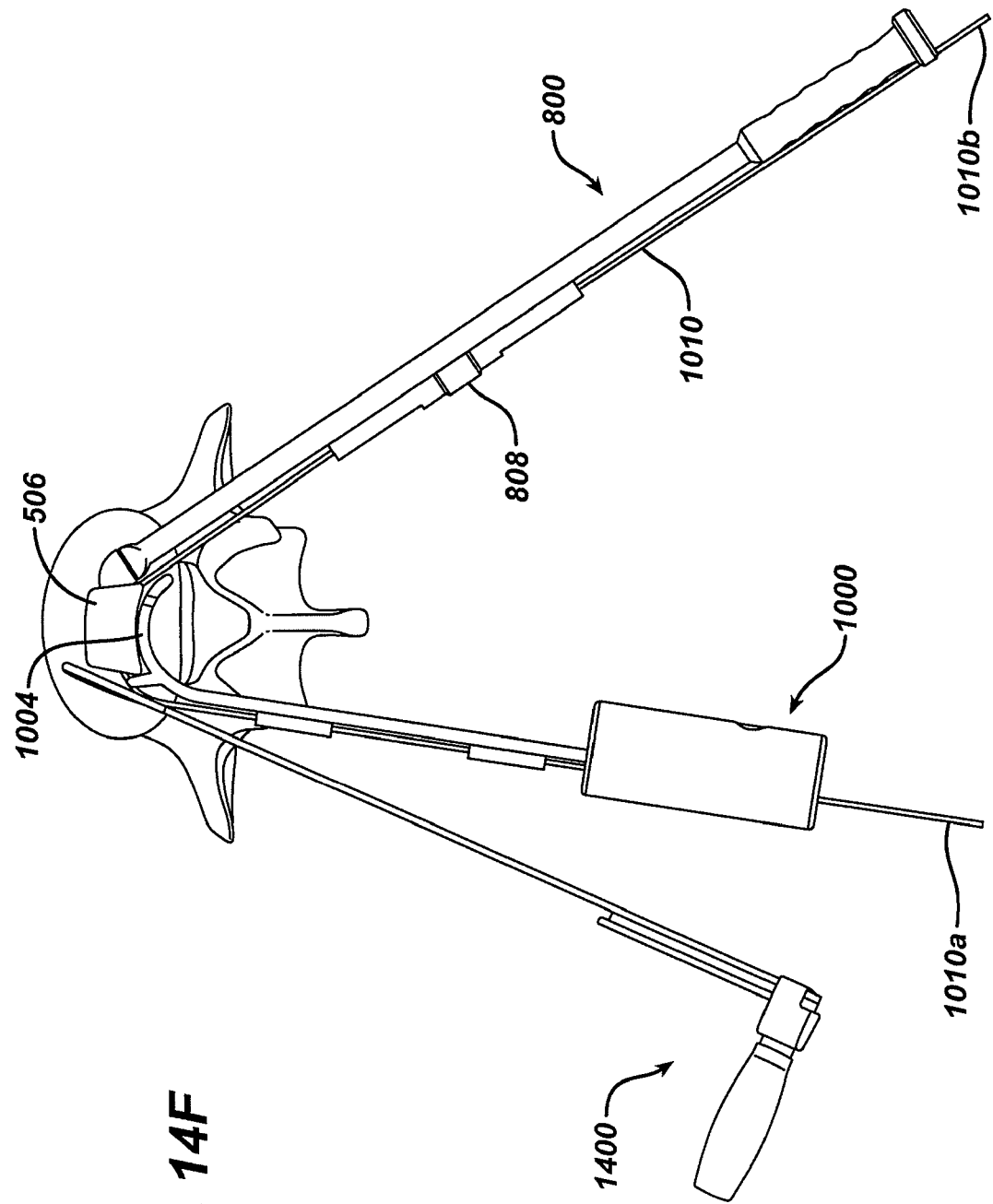
FIG. 14F is a top perspective view of the vertebra of FIG. 14D showing the central component positioned within the disc space.

Once the central component 506 is properly positioned within the disc space, as shown in FIG. 14F, the guidewire inserter tool 1000 can be removed to allow a first lateral inserter tool to be inserted. Prior to removing the guidewire inserter tool 1000, the guidewire 1010 is preferably mated or locked to the central inserter tool 800. While various locking techniques can be used, in one embodiment the central inserter tool 800 can include a set screw (not shown) disposed through the guide tube 808 and adapted to engage the guidewire 1010 when threaded into the guide tube 808. Prior to removing the guidewire inserter tool 1000, the set screw or other locking mechanism on the guidewire inserter tool 1000 may need to be released to allow slidably movement of the guidewire inserter tool 1000 relative to the guidewire 1010. During removal, the free end 1010a of the guidewire 1010 is preferably tensioned to maintain engagement with the central component 506.

Figure 14G:
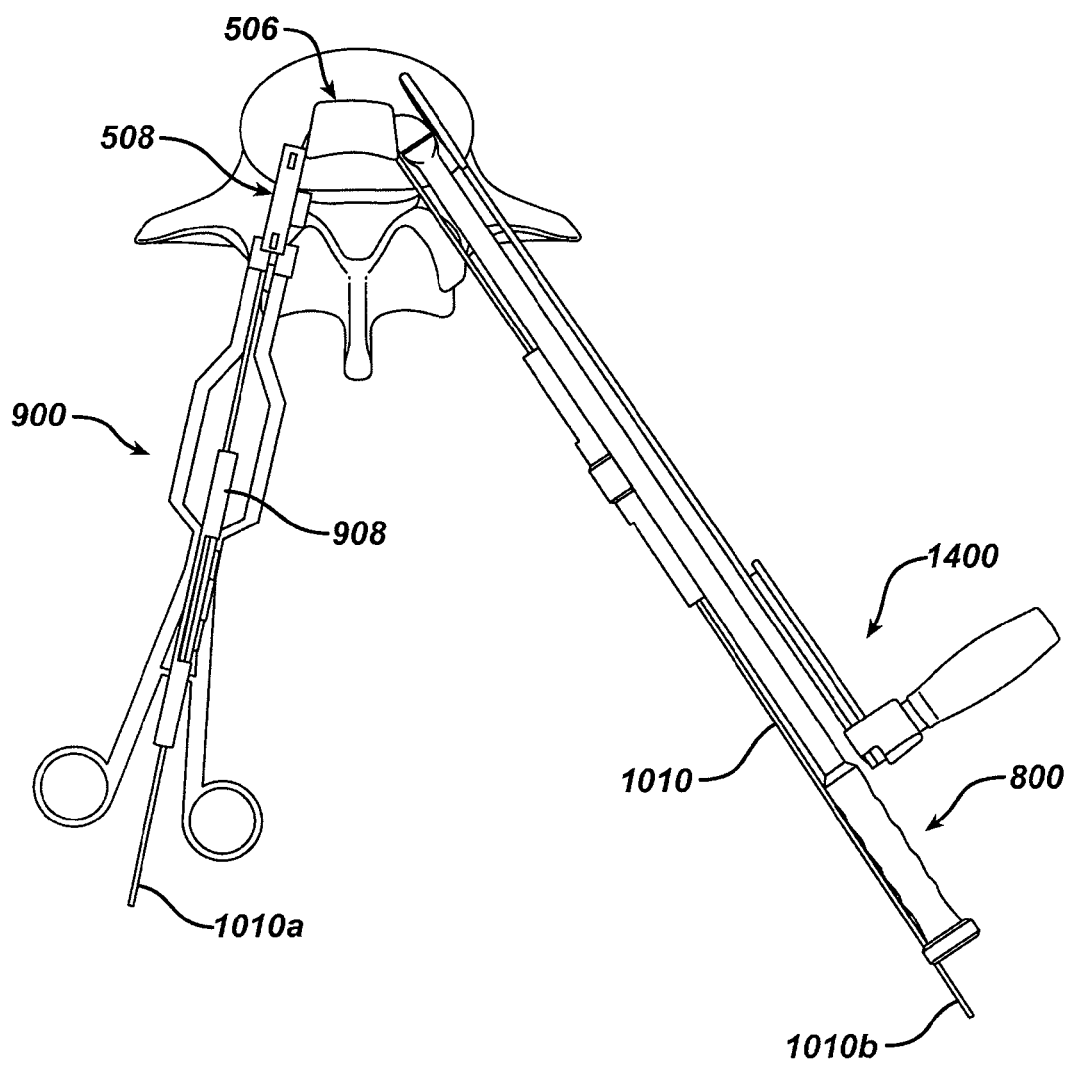
FIG. 14G is a top perspective view of the vertebra of FIG. 14F, showing the guidewire inserter tool removed and showing the lateral inserter tool of FIG. 9A being advanced along the guidewire to mate the lateral component to the central component.

The free end 1010a of the guidewire 1010 can then be threaded between the lateral members 508a, 508b of the first lateral component 508, and up through the guide tube 908 on the first lateral inserter tool 900. The lateral inserter tool 900 can be advanced along the guidewire 1010, while maintaining tension on the guidewire 1010, to enter the disc space on the contralateral side of the central inserter tool 800, thereby inserting the first lateral component 508 into the disc space, as shown in FIG. 14G. The guidewire 1010 will align the lateral component 508 with the central component 506, thereby allowing the tongues 522a, 522b on the lateral members 508a, 508b to be easily slid into the corresponding grooves 518a, 518b in the central members 506a, 506b to mate the first lateral component 508 to the central component 506. A person skilled in the art will appreciate that, while FIG. 14G illustrates the distractor 1400 positioned on a contralateral side of the disc space, as compared to FIGS. 14A-14F, the distractor 1400 can remain in its initial position throughout the entire procedure, or it can be removed or repositioned at any stage in the procedure.

Figure 14H:
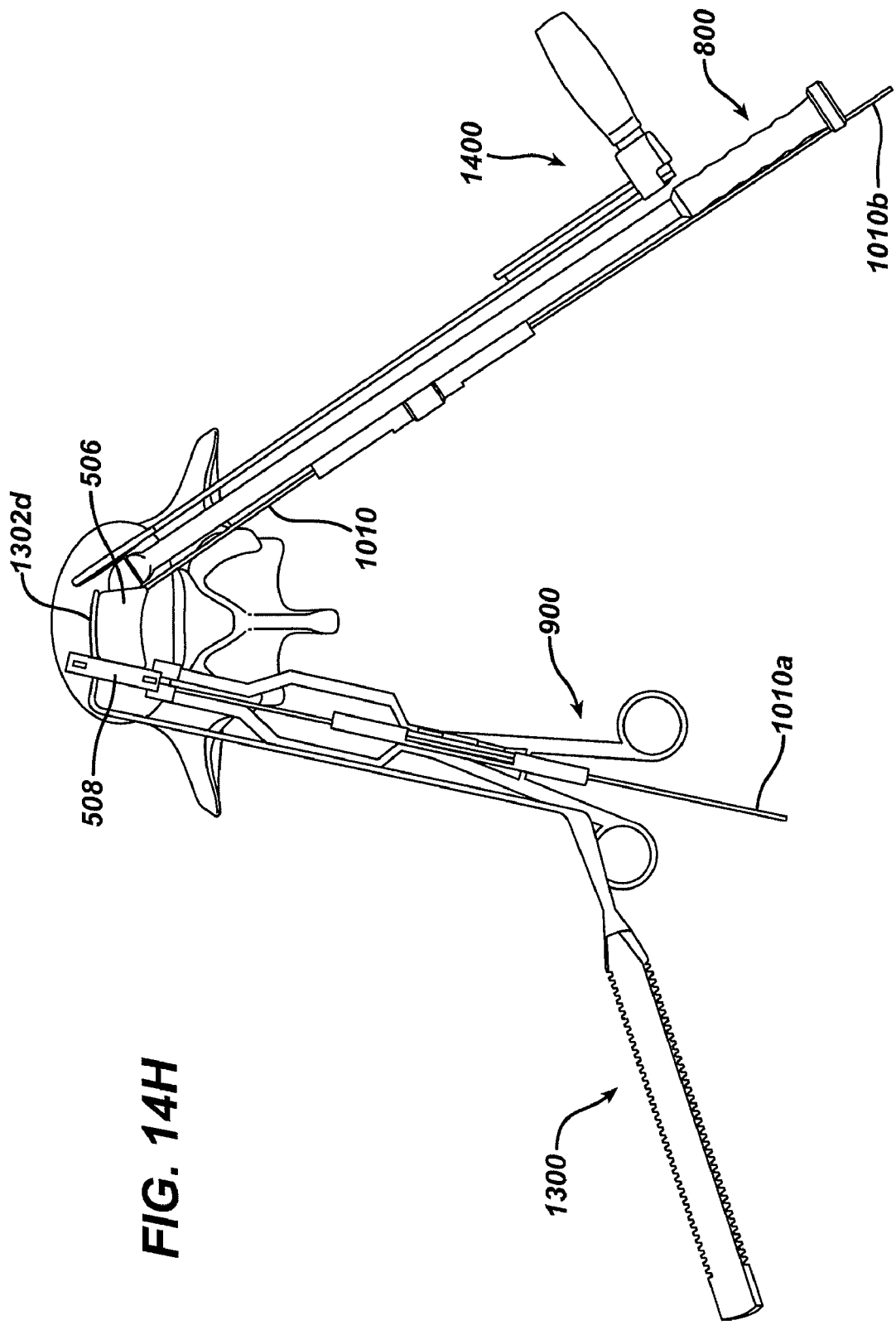
FIG. 14H is a top perspective view of the vertebra of FIG. 14G, showing the lateral component mated the central component, and showing the retaining tool of FIG. 13 positioned against the central component.

Once the first lateral component 508 is mated to the central component 506, a retaining element can optionally be used to maintain the central component 506 in a fixed position, thereby allowing for removal of the central inserter 800. FIG. 14H illustrates the distal end 1302d of retaining tool 1300 positioned against an anterior surface of the central component 506. As previously explained, in an exemplary embodiment the distal end 1302d is configured to be positioned within a gap between the central members 506a, 506b to maintain the central members 506a, 506b at a predetermined position relative to one another (i.e., to prevent movement of the central members 506a, 506b relative to one another).

Figure 14I:
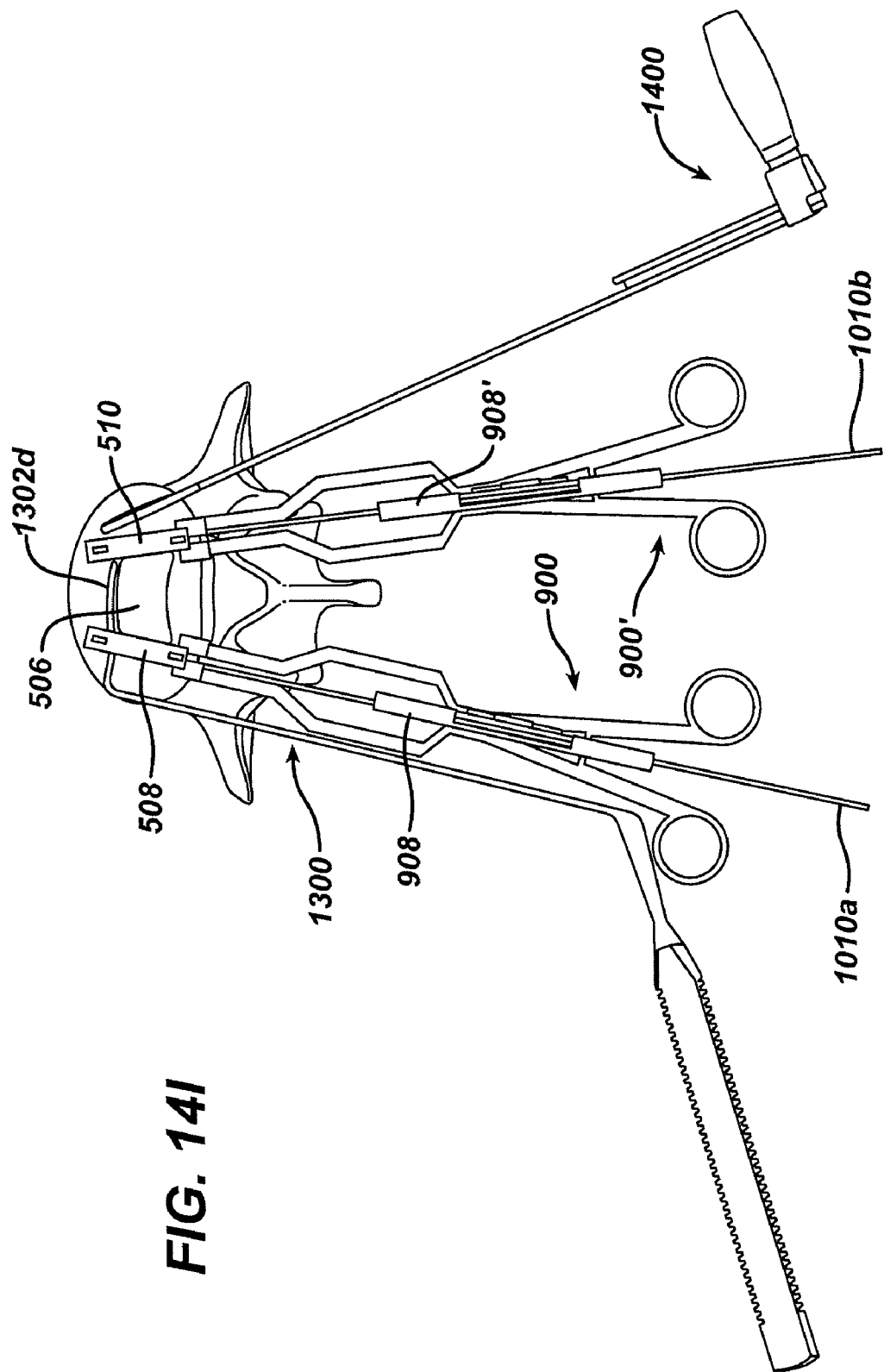
FIG. 14I is a top perspective view of the vertebra of FIG. 14H, showing the central inserter tool removed, and showing a second lateral inserter tool advanced along the guidewire on the contralateral side of the vertebra to mate a second lateral component to the central component.

With the retaining tool 1300 in place, if used, the central inserter tool 800 can be disengaged from the central component 506 and removed from the disc space. Prior to removing the central inserter tool 800, the guidewire 1010 can optionally be fixed or locked to the first lateral inserter tool 900 to maintain the guidewire 1010 in a fixed position during removal of the central inserter tool 800. This can be achieved using various locking techniques, such as a set screw disposed through the guide tube 908 on the lateral inserter tool 900 to engage the guidewire 1010. With the guidewire 1010 mated to the lateral inserter tool 900, and tension maintained on the other free end 1010b of the guidewire 1010, the central inserter tool 800 can be slid off of the guidewire 1010. A second lateral inserter tool 900 can then be threaded onto the free end 1010b of the guidewire 1010 that was just removed from the central inserter tool 800. In particular, the free end 1010b can be passed through the second lateral component 510 and through the guide tube 908' on the second lateral inserter tool 900'. The second lateral inserter tool 900' can then be advanced along the guidewire 1010, preferably while maintaining tension on the guidewire, to insert the distal end of the second lateral inserter tool 900' into the disc space on the contralateral side of the first lateral inserter tool 900, as shown in FIG. 14I. The guidewire 1010 will guide the second lateral component 510 into mating alignment with the central component 506, thereby allowing the two components 510, 506 to be easily mated to one another.

As can be appreciated from the embodiment shown in FIGS. 14A-14I, the various tools and the implant remain interconnected by the guidewire 1010 throughout the procedure. This allows the lateral components 508, 510 to be guided into mating alignment with the central component 506 without the need for visual access to the disc space. For example, as can be seen in FIG. 14G, the central inserter tool 800, central component 506, and lateral inserter tool 900 are all interconnected by the guidewire 1010. The components are thus "docket" relative to one another.

Figure 15A:
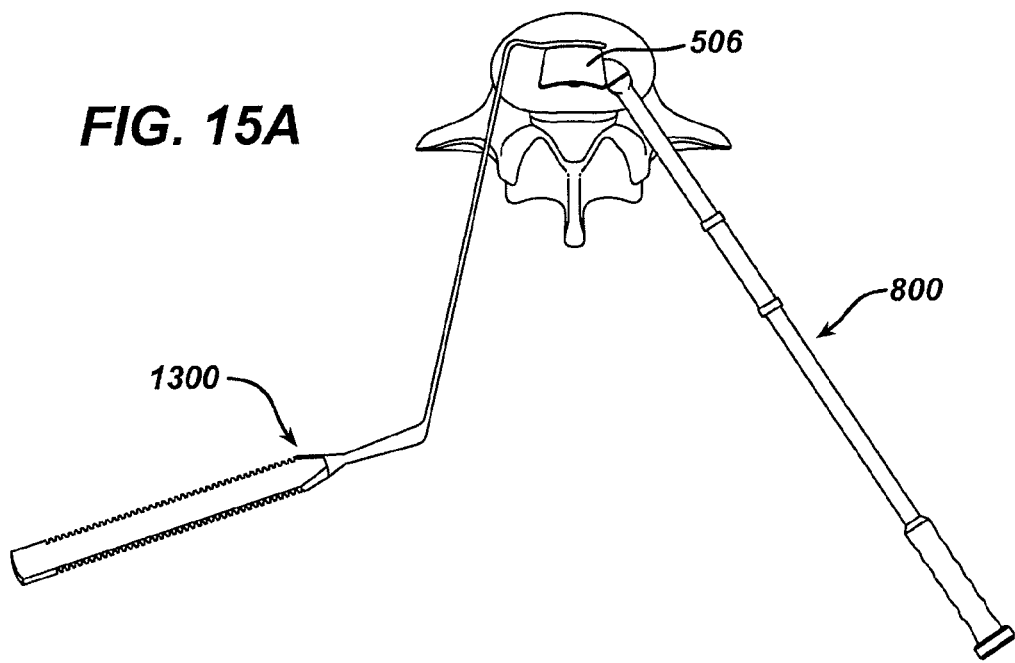
FIG. 15A is a top perspective view of a vertebra, showing the central inserter tool and central component of FIG. 8A positioned within the disc space and having the retaining tool of FIG. 13 positioned against an anterior side thereof.
Figure 15B:
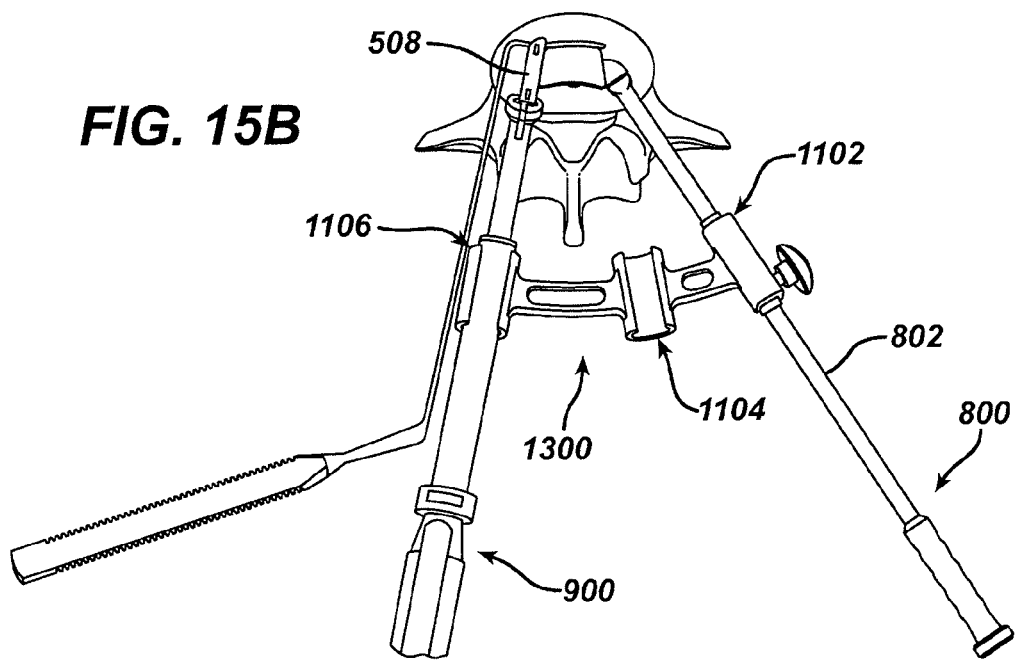
FIG. 15B is a top perspective view of the vertebra of FIG. 15A, showing a guide frame mated to the central inserter tool, and showing a first lateral inserter tool inserted through the frame for mating a first lateral component to the central component.
Figure 15C:
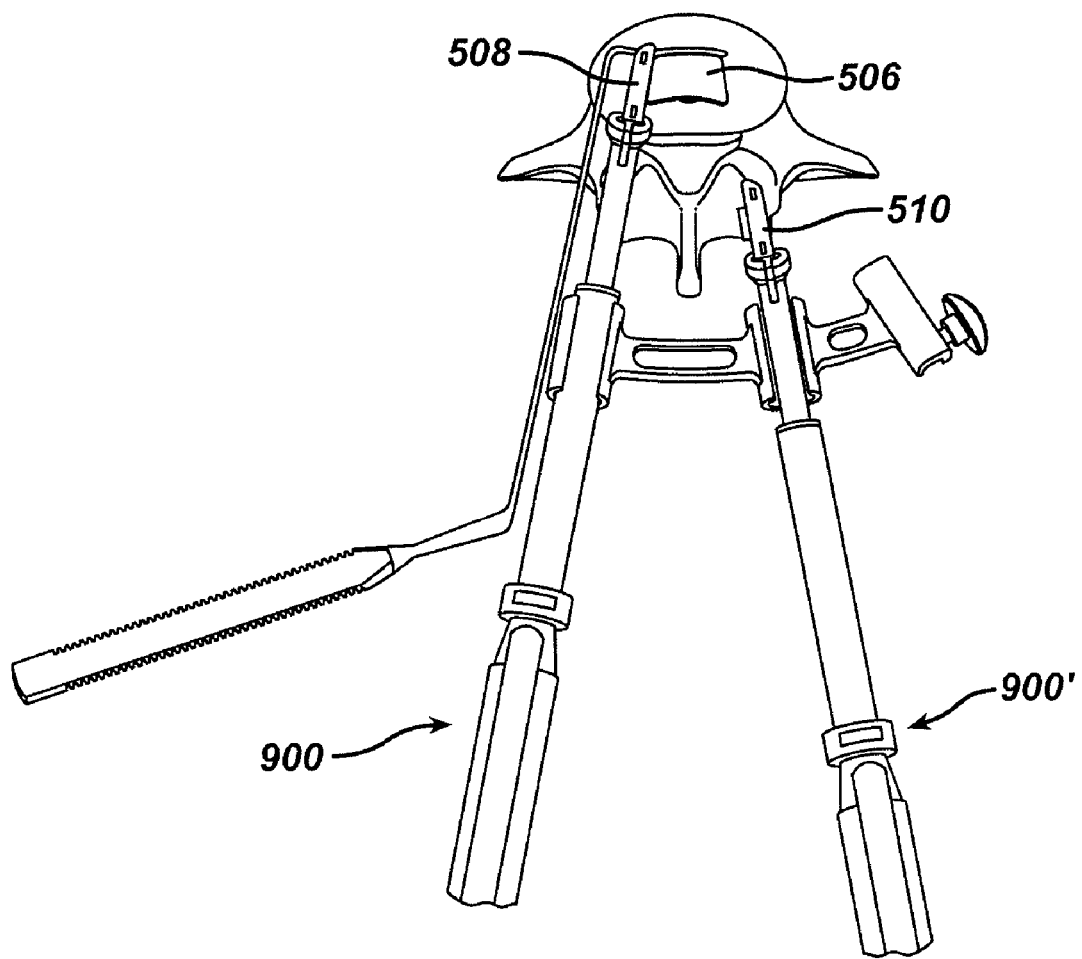
FIG. 15C is a top perspective view of the vertebra of FIG. 15B, showing the central inserter tool detached from the frame and the central component, and showing a second lateral inserter tool inserted through the frame for mating a second lateral component to the central component.

FIGS. 15A-15C illustrate another exemplary method for intraoperatively mating a multi-piece implant within a disc space. The procedure is similar to the procedure shown in FIGS. 14A-14I, except that the guide in this embodiment is the frame 1100 of FIG. 11, rather than a guidewire. Like the guidewire, the frame 1100 interconnects the various components during the procedure to allow for easy guidance of the implant components into mating alignment with one another. A person skilled in the art will appreciate that, while the method is described in connection with implant 500 and with the various tools previously discussed, the method can be used with any implant and using any tools.

As shown in FIG. 15A, the central inserter tool 800 can be inserted into the disc space on a first lateral side of the vertebra to position the central component 506 within the disc space. Fluoroscopy or other imaging techniques can be used to verify and/or adjust the position of the central component 506. Once properly positioned, the distal end 1302d retaining element 1300 can be positioned against the anterior side of the central component 506 to help maintain the central component 506 in a fixed position. The frame 1100 can be connected to the shaft 802 of the central inserter tool 800, either before or after insertion of the tool 800 into the disc space, as shown in FIG. 15B. In particular, the shaft 802 can be seated within the first channel 1102 and the locking screw 1102s can be tightened to lock the frame 1100 onto the shaft 802. The second and third channels 1104, 1106 will thus be positioned to guide the first and second lateral components 508, 510 into mating alignment with the central component 506. In particular, each channel 1104, 1106 will set the trajectory of the tools passed therethrough so that the lateral components on the tools will be pre-aligned with the central component. As shown in FIG. 15B, the first lateral inserter tool 900 can be advanced through the second channel 1106 to cause the first lateral component 508 to slide into and mate with the central component 506. After removing the central inserter tool 800, a second lateral inserter tool 900' can likewise be advanced through the first channel 1104 to cause the second lateral component 510 to slide into and mate with the contralateral side of the central component 506, as shown in FIG. 15C. The frame 1100 is therefore effective to interconnect the various tools with the central component, thereby maintaining proper alignment of all instruments and components with the central component for easy assembly within the disc space. Once the implant is fully assembly, the tools can be removed leaving the implant within the disc space.

Figure 16A:
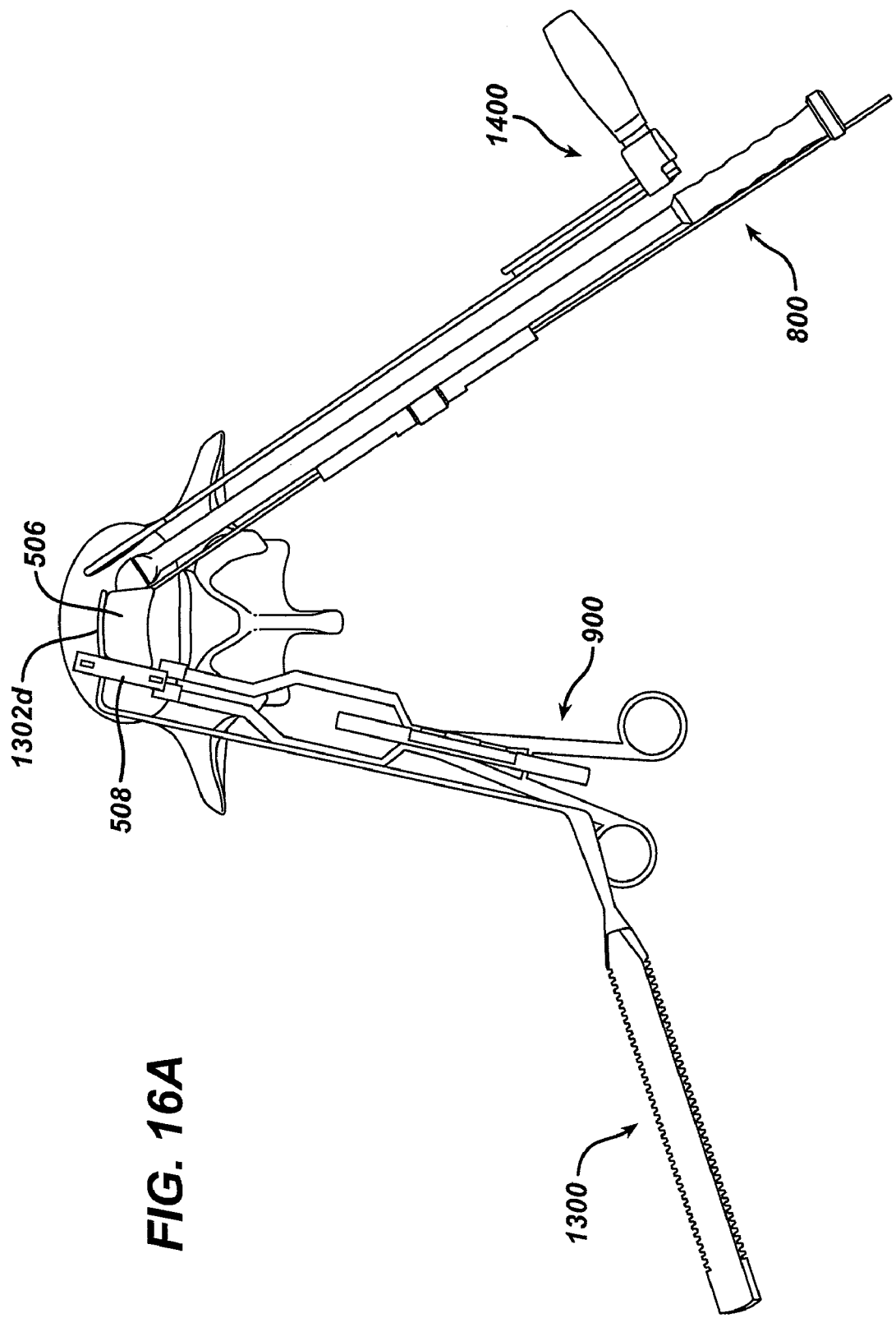
FIG. 16A is a top perspective view of a vertebra, showing a distractor, the central inserter tool and central component of FIG. 8A, the lateral inserter tool and lateral component of FIG. 9A, and the retaining tool of FIG. 13 positioned within the disc space using a wireless technique.
Figure 16B:
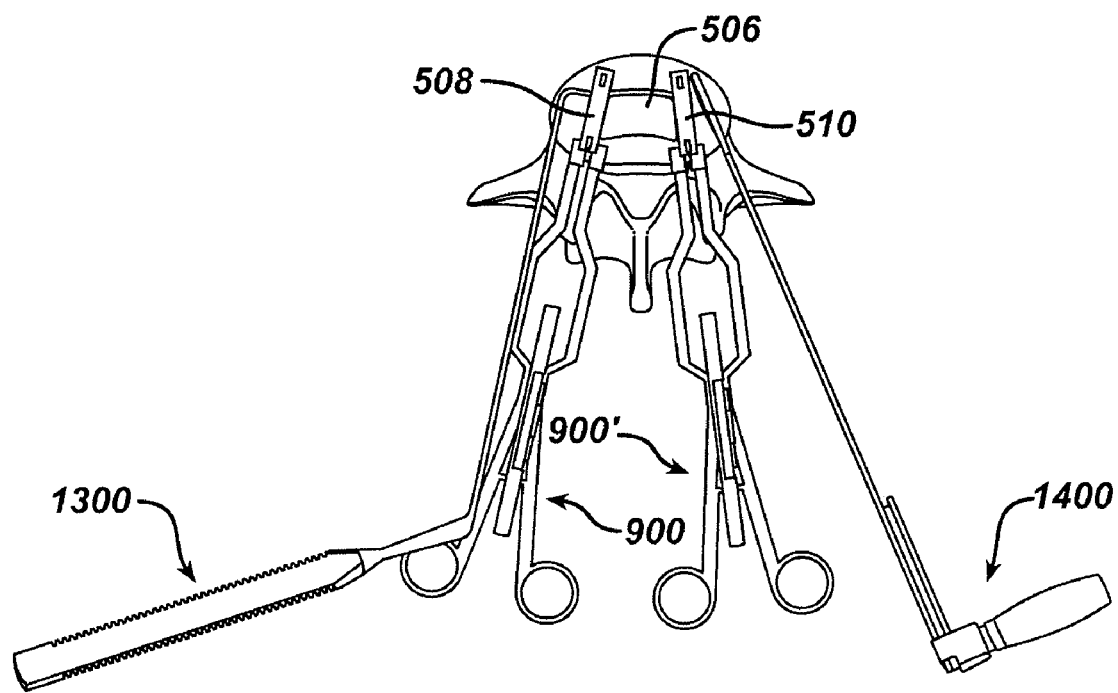
FIG. 16B is a top perspective view of the vertebra of FIG. 16A, showing the central inserter tool removed, and showing a second lateral inserter tool inserted into the disc space to mate a second lateral component to the central component.
Figure 16C:
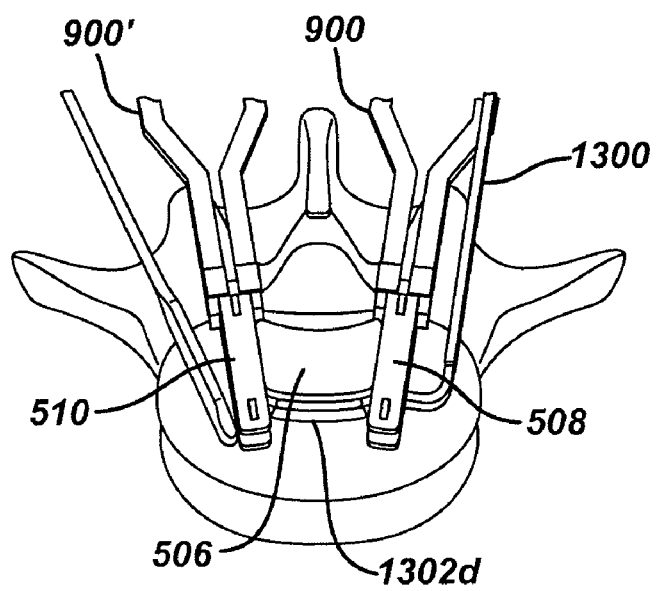
FIG. 16C is an enlarged view of the vertebra and system of FIG. 16A.

In another embodiment, as shown in FIGS. 16A-16C, the implant 500 can be implanted using a wireless technique that utilizes a procedure similar to the procedure described above, except that the components are not guided along a guidewire. In particular, as shown in FIG. 15A, after distracting the disc space using a distractor 1400 and preparing the disc space, the central inserter tool 800 can be manipulated to position the central component 506 within the disc space. Since the guidewire inserter tool is not used, various imaging techniques can optionally be used to facilitate proper positioning of the central component 506. Once positioned within the disc space, the lateral inserter tool 900 can be introduced into the disc space on the contralateral side of the central inserter tool 800. Tactile feel and/or imaging can be used to guide the first lateral component 508 into mating engagement with the central component 506. The retaining tool 1300 can also be inserted on the contralateral side of the central inserter tool 800 to position the distal end 1302d against an anterior edge of the central component 506, thereby maintaining the central component 506 in a fixed position. With the retaining element 1300 in place, the central inserter tool 800 can be removed, allowing a second lateral inserter tool 900' to be inserted along the pathway from which the central inserter tool 800 was removed. The second lateral inserter tool 900' can be manipulated to guide the second lateral component 510 into mating engagement with the central component 506, as shown in FIG. 15B. Once all components are mated, as shown in more detail in FIG. 15C, the tools can be removed leaving the implant 500 in place.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for implanting a spinal implant, comprising:
   manipulating a first inserter tool to position a first component of a spinal disc implant within a disc space between adjacent vertebrae;
   advancing a second inserter tool along a guide that is coupled to at least one of the first inserter tool and the first component such that a second component mated to the second inserter tool is guided into mating alignment with the first component to thereby mate the second component to the first component;
   detaching and removing the first inserter tool from the first component, and subsequently advancing a third inserter tool along the guide such that a third component mated to the third inserter tool is guided into mating alignment with the first component to thereby mate the third component to the first component.

2. The method of claim 1, wherein the guide comprises a guidewire coupled to the first inserter tool, the first component, and the second inserter tool, and wherein the second inserter tool is slid along the guidewire.

3. The method of claim 1, wherein the guide comprises a frame coupled to the first inserter tool, and wherein the second inserter tool is advanced through an opening in the frame.

4. The method of claim 3, wherein the frame is positioned at least partially outside of the disc space.

5. The method of claim 1, wherein the first inserter tool is inserted into the disc space on a posterolateral side of the disc space, and the second inserter tool is inserted into the disc space on a contralateral side of the disc space.

6. The method of claim 1, wherein the second component is mated to a lateral side of the first component, and the third component is mated to a contralateral side of the first component.

7. The method of claim 1, wherein the first component includes superior and inferior members that are positioned adjacent to superior and inferior endplates of the adjacent vertebrae and that are movable relative to one another.

8. The method of claim 1, wherein the second component includes superior and inferior members that are positioned adjacent to superior and inferior endplates of the adjacent vertebrae.

9. A method for implanting an artificial disc replacement, comprising:
    introducing a guidewire into a disc space and positioning the guidewire such that first and second ends of the guidewire are positioned outside of the disc space and a u-shaped portion is positioned in the disc space;
    advancing a central inserter tool along the first end of the guidewire into the disc space between adjacent vertebrae to position a central component mated to the central inserter tool within the disc space;
    advancing a first lateral inserter tool along the second end of the guidewire into the disc space to mate a first lateral component mated to the first lateral inserter tool to a first lateral side of the central component.

10. The method of claim 9, further comprising, prior to inserting the first lateral inserter tool into the disc space, positioning a retaining tool against the central component to maintain the central component in a substantially fixed position and detaching and removing the central inserter tool from the central component.

11. The method of claim 9, wherein the central inserter tool is inserted into the disc space on a posterolateral side of the disc space, and the first lateral inserter is inserted into the disc space on a contralateral side of the disc space.

12. The method of claim 9, wherein the central inserter tool is used to maintain the central component in a substantially fixed position while the first lateral component is mated to the central component.

13. The method of claim 9, wherein the guidewire is introduced into the disc space using a guidewire inserter, and the guidewire is positioned by grasping one of the first and second ends of the guidewire located in the disc space with a grasper, and pulling the grasped end of the guidewire out of the disc space.

14. A spinal implant and instrumentation system, comprising:
    an implant configured to be positioned within a disc space between adjacent vertebrae and having a central component, a first lateral component that is removably matable to a first lateral side of the central component, and a second lateral component that is removably matable to a second lateral side of the central component;
    a central inserter tool configured to removably mate to the central component;
    a first lateral inserter tool configured to removably mate to the first lateral component;
    a second lateral inserter tool configured to removably mate a second lateral component to the central component; and
    a guide frame configured to removably interconnect the implant, the central inserter tool, the first lateral inserter tool, and the second lateral inserter tool to allow the first and second lateral components to be intraoperatively guided into alignment with and mated to the first and lateral sides of the central component, the guide frame having a first channel adapted to removably receive the central inserter tool, a second channel adapted to removably receive the first lateral inserter tool, and a third channel adapted to removably receive the second lateral inserter tool.

15. The system of claim 14, wherein the first and second channels on the guide frame are positioned so as to align the central inserter tool with a first lateral side of a disc space and the lateral inserter tool with a contralateral side of the disc space.

16. The system of claim 15, wherein the second and third channels in the guide frame are positioned so as to align the first lateral inserter tool and a second lateral inserter tool with first and second opposed lateral sides of the central component.

17. The system of claim 14, wherein the central inserter tool is removably matable to the second lateral side of the central component.

18. The system of claim 14, wherein the central component includes superior and inferior members that are configured to be positioned adjacent to superior and inferior endplates of the adjacent vertebrae and that are movable relative to one another.

19. The method of claim 18, wherein the first lateral component includes superior and inferior members that are positioned adjacent to superior and inferior endplates of the adjacent vertebrae.

* * * * *